US006828416B1

(12) United States Patent
Lal et al.

(10) Patent No.: US 6,828,416 B1
(45) Date of Patent: Dec. 7, 2004

(54) RECOMBINANT MULTIVALENT MALARIAL VACCINE AGAINST *PLASMODIUM FALCIPARUM*

(75) Inventors: Altaf A. Lal, Atlanta, GA (US); Ya Ping Shi, Atlanta, GA (US); Seyed E. Hasnain, New Delhi (IN)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/763,397

(22) PCT Filed: Aug. 19, 1999

(86) PCT No.: PCT/US99/18869

§ 371 (c)(1),
(2), (4) Date: Feb. 16, 2001

(87) PCT Pub. No.: WO00/11179

PCT Pub. Date: Mar. 2, 2000

Related U.S. Application Data

(60) Provisional application No. 60/097,703, filed on Aug. 21, 1998.

(51) Int. Cl.$^7$ .......................... C07K 7/00; C07K 16/00; A61K 39/395; A61K 39/40; A61K 39/00

(52) U.S. Cl. ................. 530/300; 530/388.6; 424/139.1; 424/151.1; 424/185.1; 424/191.1; 424/265.1

(58) Field of Search .............................. 530/300, 388.6; 424/139.1, 151.1, 185.1, 191.1, 265.1, 268.1, 269.1, 272.1

(56) References Cited

U.S. PATENT DOCUMENTS

| | | |
|---|---|---|
| 4,735,799 A | 4/1988 | Patarroyo |
| 4,956,449 A | 9/1990 | Verdini et al. |
| 4,957,738 A | 9/1990 | Patarroyo |
| 4,978,621 A | 12/1990 | Ardeshir et al. |
| 4,997,647 A | 3/1991 | Nussenzweig et al. |
| 5,147,788 A | 9/1992 | Page et al. |
| 5,231,168 A | 7/1993 | Dziegiel et al. |
| 5,456,911 A | 10/1995 | James et al. |
| 5,502,168 A | 3/1996 | Kumar |
| 5,609,872 A | 3/1997 | Ahlborg et al. |
| 5,720,959 A | 2/1998 | Holder et al. |
| 5,766,597 A | 6/1998 | Paoletti et al. |

FOREIGN PATENT DOCUMENTS

| | | |
|---|---|---|
| EP | 0250261 | 12/1987 |
| WO | WO 9118922 | 12/1991 |
| WO | PCT/US96/05798 | 4/1996 |
| WO | PCT/GB98/01681 | 6/1998 |

OTHER PUBLICATIONS

Tine et al, Infection and Immunity, Sep. 1996, p. 3833–3844.*
Gilbert et al, Nature Biotechnology, vol. 15, Nov. 1997, p. 1280–1284.*
Schmitt et al, Molecular Biology Reports vol. 18, 1993, p. 223–230.*
Tine et al, Infection and Immunity, Sep. 1996, 3833–3844.*
Schmitt et al, Molecular Biology Reports, 18: 223–230, 1993.*
Gilbert et al, Nature Biotechnology, vol. 15, Nov. 1997.*
Shi et al, Proc. Natl. Acad. Sci, USA, Feb. 1999.*
Szarfman et al, Parasite Immunol. 1988, 10:339–351.*
Valero et al, The Lancet, vol. 341, No. 8847, Mar. 1993.*
Noya et al, The Journal of Infectious Diseases, 1994:170, p. 396–402.*
Patarroyo et al, Nature, vol. 328, Aug. 1987.*
Shi et al., "Immunogenicity and in vitro protective efficacy of a recombinant multistage *Plasmodium falciparum* candidate vaccine," *Proc. Natl. Acad. Sci. USA*, 96(4):1615–1620, Feb. 1999.
Gilbert et al., "A protein particle vaccine containing multiple malaria epitopes," *Nature Biotech.*, 15:1280–1284, Nov. 1997.
Mason et al., "Production of Monoclonal Antibodies for Immunocytochemical Use," in *Techniques in Immunocytochemistry*, Bullock and Petrusz (eds.), Academic Press 1983, pp. 175–216.
*Immunology*, Hood et al, (ed.), The Benjamin/Cummings Publishing Company, Inc., pp. 66 and 74, 1984.
Rzepczyk et al., "Synthetic peptide immunogens eliciting antibodies to *Plasmodium falciparum* sporozoite and merozoite surface antigens in H–$2^b$ and H–$2^k$ mice," *J. Immunol.* 145:2691–2696, Oct. 15, 1990.
Sturchler et al., "Safety, immunogenicity, and pilot efficacy of *Plasmodium falciparum* sporozoite and asexual blood–stage combination vaccine in Swiss adults," *Am. J. Trop. Med. Hyg.* 52:423–431, 1995 (first page only).

(List continued on next page.)

*Primary Examiner*—Nita Minnifield
*Assistant Examiner*—Vanessa L Ford
(74) *Attorney, Agent, or Firm*—Klarquist Sparkman LLP

(57) ABSTRACT

A recombinant protein is provided which comprises peptides derived from different stages in the life cycle of parasite *Plasmodium falciparum*. The protein is useful as a reagent and, when combined with a pharmaceutically-acceptable vehicle or carrier, is useful as a vaccine against the material parasite *Plasmodium falciparum*. A genetic construct used to produce this recombinant protein vaccine is also described. In addition, antibodies to this recombinant protein are provided which are useful for the detection and measurement of peptides derived from different stages in the life cycle of the parasite *Plasmodium falciparum*.

7 Claims, 5 Drawing Sheets

OTHER PUBLICATIONS

Szarxman et al., "Mature liver stages of cloned *Plasmodium falciparum* share epitopes with proteins from sporozoites and asexual blood stages," *Parasite Immunol.* 10:339–351, 1988 (first page only).

Tine et al., "NYVAC–Pf7: a Poxvirus–Vectored, Multiantigen, Multistage Vaccine Candidate for *Plasmodium falciparum* Malaria," *Infect. Immun.* 64:3833–3844, Sep. 1996.

Wang et al., "Protective efficacy against malaria of a combination sporozoite and erythrocytic stage vaccine," *Immun. Lett.* 53:83–93, 1996.

Reisberg, Ch. 15, "Malaria," in *The Biologic and Clinical Basis of Infectious Diseases,* Youmans et al (eds.), W.B. Saunders Company, pp. 707–716, 1982.

Szarfman et al., "Mature liver stages of cloned *Plasmodium falciparum* share epitopes with proteins from sporozoites and asexual blood stages," *Parasite Immunol.* 10:339–351, 1998 (Complete article).

* cited by examiner

FIG_1

FIG_2

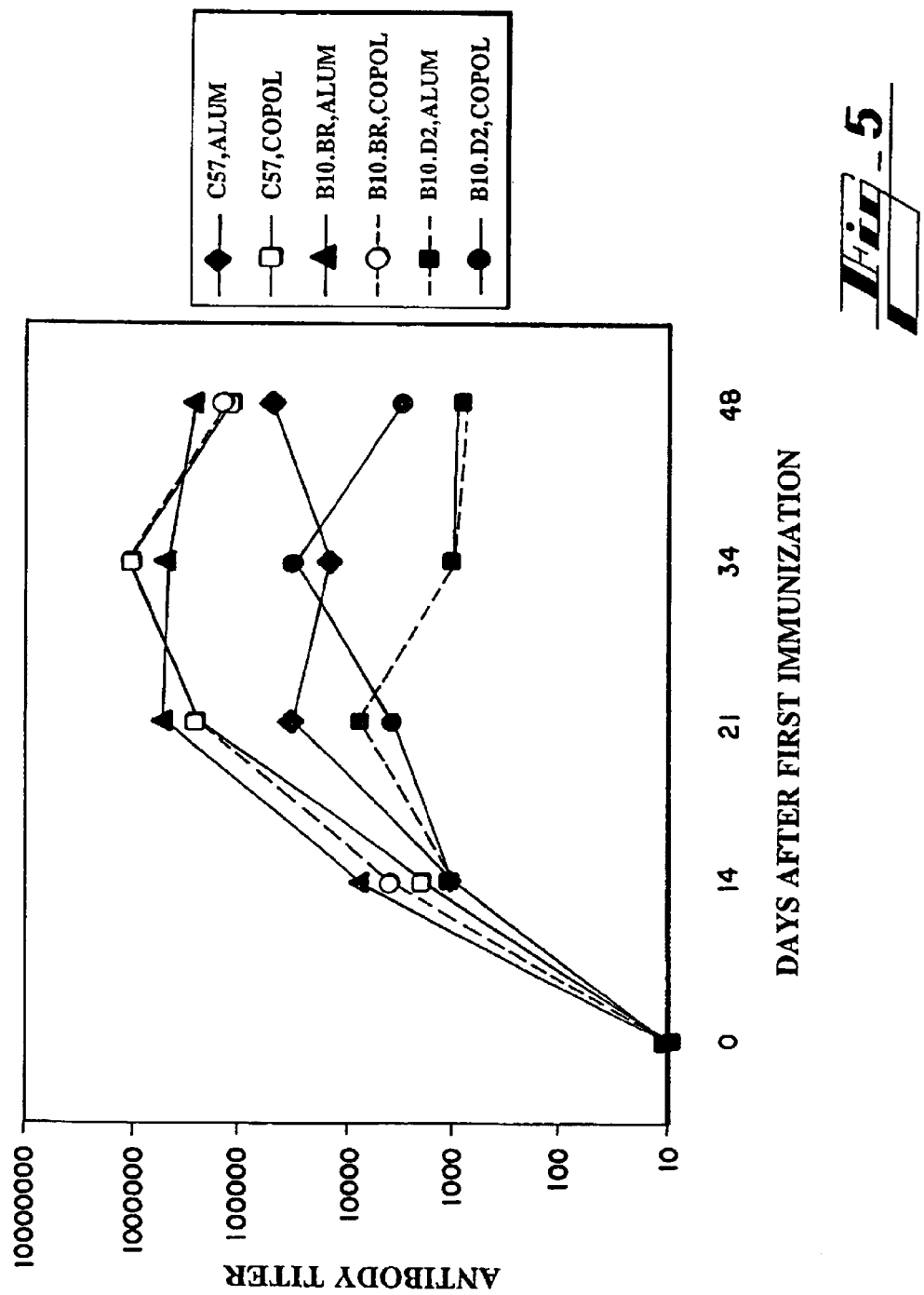

RECOMBINANT MULTIVALENT MALARIAL VACCINE AGAINST *PLASMODIUM FALCIPARUM*

REFERENCE TO RELATED CASES

This application claims priority to co-pending International Application Number PCT/US99/18869, filed Aug. 19, 1999, which claims the benefit of U.S. Provisional Application No. 60/097,703, filed Aug. 21, 1998.

This invention was made by the Centers for Disease Control and Prevention, an agency of the United States Government. Therefore the United States Government may have certain rights in this invention.

FIELD OF THE INVENTION

The present invention relates generally to the development and use of a gene encoding a recombinant protein useful as a multivalent and multistage malaria vaccine and more specifically relates to a recombinant antigenic protein useful for preventing or treating *P. falciparum* malarial infections.

BACKGROUND OF THE INVENTION

Malaria is a parasitic infection known to be produced by the *Plasmodium* species *P. falciparum*, *P. vivax*, *P. ovale*, and *P. malariae*. Humans become infected following the bite of an infected anopheline mosquito, the host of the malarial parasite. Malaria occasionally occurs in humans following a blood transfusion or subsequent to needle-sharing practices as used by drug addicts.

When an infected anopheline mosquito bites an individual, sporozoites present in the mosquito's saliva are injected into the blood. The initial development of parasites occurs in the liver and is referred to as the liver stage, or the hepatic or exoerythrocytic phase. In this phase, the sporozoite grows and divides, producing numerous tissue merozoites. These merozoites rupture the hepatocyte and enter the circulation. Some merozoites attach to receptor sites on red blood cells, penetrate the plasmalemma and begin a development phase known as the asexual, erythrocytic cycle. Within the erythrocyte, the parasite is recognizable as a ring-stage trophozoite. These trophozoites enlarge, divide and attain the schizont stage. After successive nuclear divisions, the erythrocyte ruptures, releasing merozoites which attach to receptors on erythrocytes and thus begin another erythrocytic cycle. In *P. vivax* and *P. ovale*, hepatic parasites persist and may lead to a relapse of the disease months or years after the initial infection.

Some merozoites that enter red blood cells develop into male and female gametocytes. When a mosquito bites an individual possessing erythrocytic gametocytes and ingests them, the gametocytes are fertilized in the stomach of the mosquito and mature into sporozoites that migrate to the salivary glands. In this manner, the mosquito is capable of biting and infecting another individual.

Malaria is one of the most common infections of humans. It is estimated that malaria parasites cause about 300–500 million illnesses and 3 million deaths each year. Most of the severe morbidity and mortality occurs in children and pregnant women, and is caused by *P. falciparum* (World Health Organization (1989) *Weekly Epidemiol. Res.* 32, 241–247). While sub-Saharan Africa accounts for more that 90% of these cases, malaria is a serious public health problem for nonimmune individuals and servicemen and servicewomen traveling through and/or stationed in malarious regions of the world. Clinical manifestations of malarial infection which may occur include blackwater fever, cerebral malaria, respiratory failure, hepatic necrosis, and occlusion of myocardial capillaries. An effective vaccine that prevents or reduces infection and minimizes morbidity and mortality will be a very useful tool for the control and prevention of this disease.

The development of an effective malaria vaccine represents one of the most promising approaches for providing cost-effective intervention along with other control measures currently available. Over the last decade there has been considerable progress in the understanding of immune mechanisms involved in protection against parasites and clinical illness. Several malarial antigens have been identified for their ability to confer protection against malaria.

Three main types of malarial vaccines are currently under research and development, based on stages of the parasite's life cycle. The three vaccines are generally directed to the following stages in the life cycle: 1) blood stage, including the asexual blood stage; 2) the sexual stages; and 3) preerythrocytic stages, including the liver stage. Antigens from each of these stages have been identified, the most promising being antigens from the following proteins: circumsporozoite protein (CSP) and SSP-2 protein of the sporozoite stage; the antigen (LSA-1) of the liver stage; the merozoite surface protein-1 (MSP-1), merozoite surface protein-2 (MSP-2), the rhoptry associated protein-1 and -2 (RAP-1 and RAP-2), the erythrocyte binding antigen-175 (EBA-175) and apical membrane antigen-1 (AMA-1) of the asexual blood stage; and the ookinete antigen Pfs 25 and the gamete specific antigen Pfg27 of the sexual stage.

Therefore, what is needed is a single vaccine that provides immunogenicity or confers immunity against various stages in the life cycle of the malarial parasite, particularly *P. falciparum*, to treat, minimize or prevent infection and reduce associated morbidity and mortality.

SUMMARY OF THE INVENTION

An antigenic recombinant protein, method of making the protein, genetic construct encoding the protein, antibodies to the protein, pharmaceutical composition containing the protein, and a method for the treatment, prevention or reduction of malarial infection by administering the protein to a human or animal are provided. The protein and anti-protein antibodies are useful as research or diagnostic reagents for the detection of the Plasmodium species *P. falciparum* in a biological sample. When administered to human or nonhuman animals, the protein is effective against malaria by conferring immunogenicity or immunity against various stages in the life cycle of the malarial parasite *P. falciparum*.

The antigenic recombinant protein is prepared by constructing a gene that encodes stage-specific antigenic determinants. The gene is added to a vector and is then expressed in a suitable expression system, such as a baculovirus system, to produce a single protein that confers immunity against different stages in the malarial life cycle of *P. falciparum*, or provides immunogenicity against epitopes from different stages in the life cycle of the parasite. In the present invention, these stages are the sporozoite stage, the liver stage, the blood stage and the sexual stage (also known as the gametocyte stage). By using a combination of antigens or epitopes derived from different stages in the life cycle of a malarial parasite, the protein constitutes an efficacious, cost-effective, and sustainable multicomponent vaccine for use in malaria control programs. The protein, in a pharmaceutically acceptable carrier, specifically provides a multivalent and multistage vaccine for malaria caused by the parasite *P. falciparum*.

The immunogenic regions of the various stage-specific antigens of *P. falciparum* used to construct the gene encoding the antigenic recombinant protein are selected based on immune response studies in clinically immune adults and in vitro immune response studies using peptides and/or antibody reagents. The resulting synthetic gene is sequence-confirmed and expressed in a baculovirus expression system. The preferred antigenic fragments used to make the coding sequences used in construction of the gene are shown in Table 1. The nucleotide sequence of the preferred gene is shown in SEQ ID NO:1. The amino acid sequence of the preferred recombinant protein encoded by the gene, referred to herein as CDC/NIIMALVAC-1, is shown in SEQ ID NO. 2. The recombinant protein in a pharmaceutically acceptable carrier is useful as a multivalent, multistage vaccine for *P. falciparum* malaria.

The vaccine described herein is a cost-effective, health-promoting intervention for controlling, preventing or treating the incidence of malaria. The vaccine is useful for reducing sickness, morbidity, mortality and the cost of medical care throughout the world. Similarly, the vaccine is useful for preventing or reducing malarial infection in U.S. citizens and military personnel traveling or living in regions of the world where malaria is present. The vaccine is also useful for decreasing the severity of the malarial disease process when administered after initial infection with *P. falciparum*.

The vaccine is immunogenic as confirmed by its ability to elicit immune responses against both the vaccine protein and the *P. falciparum* parasite. In vitro tests of protection conferred by the vaccine against blood stage malarial parasites reveal that antibodies against this vaccine inhibit reproductive growth of *P. falciparum*. The vaccine also induces multiple layers of immunity to different stages in the parasitic life cycle of *P. falciparum*.

It is therefore an object of the present invention to provide a multivalent, multistage vaccine against malaria.

Another object of the present invention is to provide a multivalent, multistage vaccine against malaria caused by *P. falciparum*.

Yet another object of the present invention is to provide a vaccine against malaria that is effective in inhibiting reproductive growth of the parasite within a human or animal after initial infection.

Still another object of the present invention is to provide a gene useful as a DNA vaccine, or for production of a recombinant protein in various expression systems, the recombinant protein containing antigenic epitopes to various stages of a malarial *Plasmodium* species, particularly *P. falciparum*.

Another object of the present invention is to provide a vector comprising a gene useful for production of a recombinant protein in various expression systems, the protein containing antigenic epitopes to various stages of a malarial *Plasmodium* species, particularly *P. falciparum*. This vector may be used for a variety of purposes including but not limited to administration to animals and humans, and for transfection of cells.

Yet another object of the present invention is to provide a recombinant protein containing antigenic epitopes to various stages of *P. falciparum* that may be used as a reagent or a multivalent, multistage antimalarial vaccine.

It is another object of the present invention to provide a method for conferring immunity against different stages in the life cycle of the malarial parasite, *P. falciparum*.

Another object of the present invention is to provide a method of vaccination against malaria caused by infection with *P. falciparum*.

It is another object of the present invention to provide a method to reduce morbidity and mortality associated with malarial infection by preventing malarial infection and also ameliorating the morbidity and mortality associated with malaria after initial infection with the parasite, *P. falciparum*.

Another object of the present invention is to provide antibodies against a recombinant protein containing antigenic epitopes to various stages of *P. falciparum*, that are useful as research or diagnostic reagents for the detection and measurement of *P. falciparum* in a biological sample.

Yet another object of the present invention is to provide a more effective, simpler and economical vaccine for conferring immunogenicity to different stages in the life cycle of *P. falciparum* than prior art vaccines.

An advantage of the anti-malaria vaccine of the present invention is that it confers immunogenicity against several stages or all stages in the life cycle of *P. falciparum* with administration of a single vaccine, as opposed to multiple injections for each stage of the life cycle of the parasite.

These and other objects, features and advantages of the present invention will become apparent after a review of the following detailed description of the disclosed embodiments.

BRIEF DESCRIPTION OF THE FIGURES

FIG. 5 is a graph showing the antibody response (antibody titer, log scale) to CDC/NIIMALVAC-1 in inbred mice of different genetic backgrounds as a function of time in days after the first immunization. Shown are C57 mice receiving alum (solid diamond) or copolymer (open square), B10.BR mice receiving alum (solid triangle) or copolymer (open circle), B10.D2 mice receiving alum (solid square) or copolymer (closed circle). All mice received a booster injection at 14 days.

DETAILED DESCRIPTION OF THE INVENTION

Figure 1:
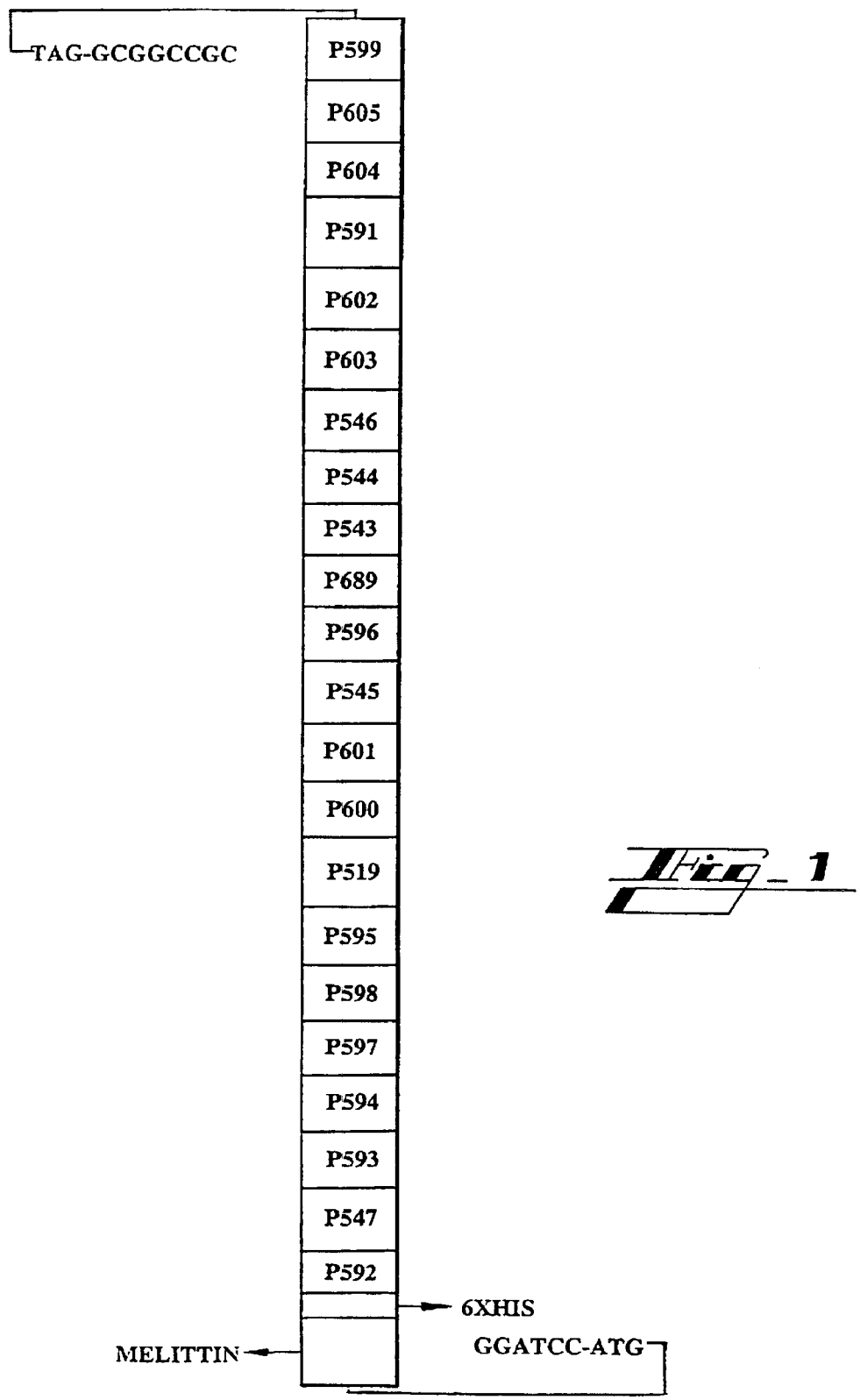
FIG. 1 is a schematic map of the synthetic gene encoding production of the recombinant protein CDC/NIIMALVAC-1. Locations of epitopes in CDC/NIIMALVAC-1 are indicated by the codes which correspond to codes in Table 1.

An antigenic recombinant protein containing immunogenic malarial epitopes from different stages of the malarial parasite life cycle; a method of making the protein, including a genetic construct from which the protein is produced; antibodies to the protein; a pharmaceutical composition containing the protein, useful as a malarial vaccine; and a method for treating, preventing or reducing malarial infection by administering the composition to a human or animal are described herein. The genetic construct includes coding sequences for different peptide fragments obtained from different stages in the life cycle of a malarial parasite, preferably *P. falciparum*. The genetic construct also includes epitopes chosen to enhance recognition by cells of the immune system of the protein expressed from the genetic construct. A preferred genetic construct includes coding sequences for a signal peptide, for a polyhistidine sequence useful for purification of the protein, a universal T-helper epitope, and at least one epitope from each stage in the life cycle of *P. falciparum*. The preferred genetic construct has the nucleotide sequence of SEQ ID NO:1, or a nucleotide sequence having conservative nucleotide substitutions, as defined in the definitions, that do not significantly alter the function of the expressed recombinant protein in an adverse manner.

The genetic construct is expressed in an expression system, such as a baculovirus expression system, to produce a recombinant protein. The preferred protein is the protein referred to herein as CDC/NIIMALVAC-1, which has the amino acid sequence set forth in SEQ ID NO:2, or an amino acid sequence having amino acid substitutions as defined in the definitions that do not significantly alter the function of the recombinant protein in an adverse manner. The protein is combined with a pharmaceutical carrier and is used as a multivalent vaccine to confer immunity to the different stages in the life cycle of the malarial parasite, *P. falciparum*, when combined with a pharmaceutically acceptable carrier and administered in an effective amount to a human or animal. The present invention specifically provides a multivalent and multistage vaccine useful for preventing and treating malaria caused by *P. falciparum*. The present invention also provides polyclonal and monoclonal anti-protein antibodies produced after immunization with the recombinant protein which are useful, as is the protein, as research or diagnostic reagents in an assay for the detection or monitoring of malarial infection, particularly to detect malarial infection caused by *P. falciparum*. The antibodies are also useful for inducing passive immunization. Some of these results have been published by Shi et al., *Proc. Natl. Acad. Sci. USA* 96:1615–1620, the entirety of which is herein incorporated by reference.

Definitions

The terms "a", "an" and "the" as used herein are defined to mean one or more and include the plural unless the context is inappropriate.

The term "multivalent" as used herein is defined to mean more than one epitope.

The term "multistage" as used herein is defined to mean more than one stage in the life cycle of *P. falciparum*. These stages include the sporozoite stage, the liver stage, the blood stage and the sexual stage.

"Peptides", "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that individual substitutions, deletions or additions in the amino acid sequence of the protein, or in the nucleotide sequence encoding for the amino acids in the protein, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Antigenic Peptide Production

When the antigenic epitope peptides are relatively short in length (i.e., less than about 50 amino acids), they are often synthesized using standard chemical peptide synthesis techniques. Solid phase synthesis, in which the C-terminal amino acid of the sequence is attached to an insoluble support followed by sequential addition of the remaining amino acids in the sequence, is a preferred method for the chemical synthesis of the antigenic epitopes described herein. Techniques for solid phase synthesis are known to those skilled in the art.

Alternatively, the antigenic epitopes described herein are synthesized using recombinant nucleic acid methodology. Generally, this involves creating a nucleic acid sequence that encodes the peptide or polypeptide, placing the nucleic acid in an expression cassette under the control of a particular promoter, expressing the peptide or polypeptide in a host, isolating the expressed peptide or polypeptide and, if required, renaturing the peptide or polypeptide. Techniques sufficient to guide one of skill through such procedures are found in the literature.

While the antigenic epitopes are often joined directly together, one of skill will appreciate that the antigenic epitopes may be separated by a spacer molecule such as, for example, a peptide, consisting of one or more amino acids. Generally, the spacer will have no specific biological activity other than to join the antigenic epitopes together, or to preserve some minimum distance or other spatial relationship between them. However, the constituent amino acids of the spacer may be selected to influence some property of the molecule such as the folding, net charge, or hydrophobicity.

Once expressed, recombinant peptides, polypeptides and proteins can be purified according to standard procedures known to one of skill in the art, including ammonium sulfate precipitation, affinity purification through columns or other methods commonly known, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the antigenic peptide epitopes, polypeptides and proteins may possess a conformation substantially different than the native conformations of the constituent peptides. In this case, it is often necessary to denature and reduce the polypeptide and then to cause the polypeptide to refold into the preferred conformation. Methods of reducing and denaturing proteins and inducing refolding are well known to those of skill in the art.

Recombinant Protein Production

The method of producing the recombinant protein CDC/NIIMALVAC-1 involves the following steps: 1) selecting antigenic components, preferably antigenic peptides, from different stages in the life cycle of P. falciparum, that are involved in conferring immunologic protection; 2) optionally selecting a signal peptide sequence, such as melittin, optionally selecting other protein or peptide epitopes useful as T-cell helpers such as tetanus toxoid, and optionally selecting protein or peptide epitopes from P. falciparum involved in T-cell and B-cell recognition; 3) generating gene fragments comprised of nucleotide sequences that are complementary to the selected protein fragments; 4) assembling the gene fragments to create a gene, preferably a gene having the nucleotide sequence of SEQ ID NO:1, that encodes a novel recombinant protein, preferably the protein referred to herein as CDC/NIIMALVAC-1 having the amino acid sequence of SEQ ID NO:2; 5) cloning the gene into an expression vector so that it may be expressed in an expression system; and 6) expressing the recombinant protein in the expression system. The expressed recombinant protein is then recovered and purified. This protein is combined with a pharmaceutically acceptable vehicle or carrier and is administered as a multivalent, antimalarial vaccine to humans and nonhuman animals. The vaccine is administered in an amount effective to confer immunity against infection caused by P. falciparum, and particularly, to confer immunogenicity or immunity against different stages in the life cycle of P. falciparum.

Compared to vaccines directed to a single stage in the life cycle of malaria, the multivalent and multistage P. falciparum vaccine of the present invention induces multiple "layers" of immunity which significantly increase the chances of neutralizing all stages in the life cycle of the malaria parasite. The method of the present invention permits synthesis of a gene that contains coding sequences for several protective/immunodominant malarial epitopes of the malarial parasite P. falciparum.

A potential concern with the design of a synthetic gene encoding multiple epitopes is that the tandem arrangement of epitopes in the recombinant protein may induce antigenic competition, thus rendering immunizations ineffective in inducing immune responses. As shown in the examples and figures herein, the results from an immunization study involving the administration of CDC/NIIMALVAC-1 to mice and rabbits alleviate this concern. CDC/NIIMALVAC-1 is immunogenic. The recombinant protein antigen is recognized by antibodies directed against the B-cell epitopes of the construct. The vaccine is also antigenic since the immunization of rodents and rabbits induced antibodies that react with the protein vaccine, and also with the sporozoite and infected red blood cells. In addition, results of the experiments performed to evaluate the protective effects of immunization with CDC/NIIMALVAC-1 show that murine and rabbit antibodies against CDC/NIIMALVAC-1 inhibit parasite growth, as determined by the growth inhibition assay (GIA) and the antibody-dependent cellular inhibition (ADCI) assay.

The data set forth in the examples demonstrate that the protein, CDC/NIIMALVAC-1, in the multicomponent P. falciparum vaccine, induces "multiple layer" of immunity, and that anti-CDC/NIIMALVAC-1 antibodies recognize different stages of the life cycle of the malarial parasite.

Construction of the Recombinant Gene

Figure 2:
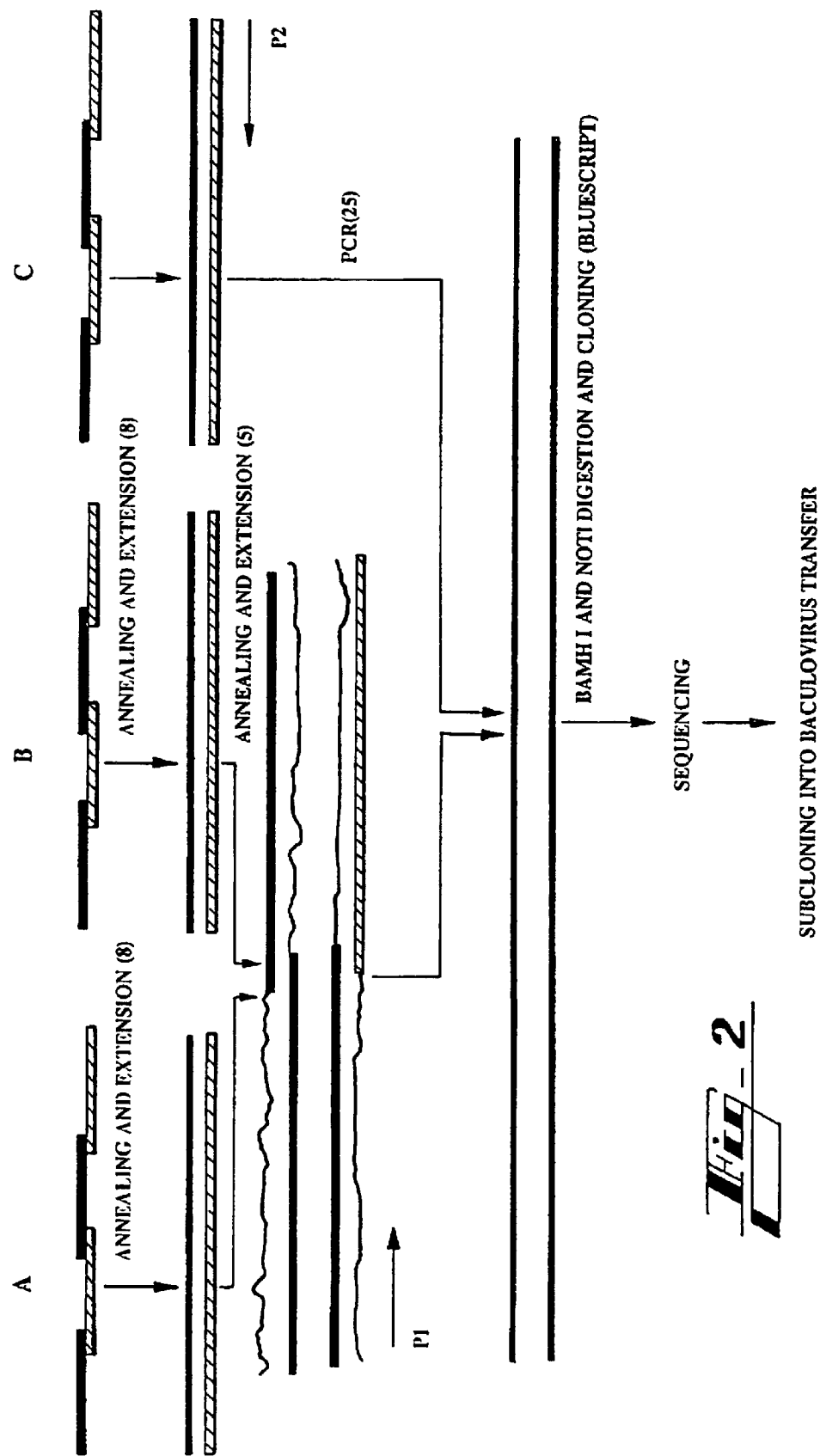
FIG. 2 is a flow chart revealing the strategy employed in the synthesis of the gene encoding production of the recombinant protein CDC/NIIMALVAC-1.

Immunogenic regions of various stage-specific antigens are identified by immune response studies in clinically immune adults and immune response studies performed in vitro using peptides and antibody reagents. Short, single-stranded DNA fragments complementary to the different epitopes are synthesized by methods known to those skilled in the art. Different DNA fragments are annealed to create a synthetic multicomponent gene by a three step polymerase chain reaction (PCR) amplification process as shown in FIG. 2. The principle behind the use of overlapping long oligonucleotides or gene fragments in the three round PCR procedure is that the sense strand and anti-sense strands of the nucleotide sequences are complementary at overlapping regions and act as primers after annealing.

Table 1 presents amino acid sequences of the twelve B-cell and nine T-cell epitopes derived from nine stage-specific vaccine candidate antigens of P. falciparum used in the development of the protein CDC/NIIMALVAC-1. One universal T-cell epitope, from tetanus toxoid is also incorporated. A sequence for the melittin signal peptide, used for enhancement of protein secretion in the baculovirus expression system, is added to the N terminus. A sequence of six histidines is inserted immediately C-terminal to the melittin signal peptide sequence to facilitate purification of expressed recombinant CDC/NIIMALVAC-1 on a nickel column. Corresponding nucleotide sequences for the melittin signal peptide sequence, the six histidine residues and the epitopes from P. falciparum are constructed. Restriction enzyme sites BamHI and NotI are designed at the flanking end to facilitate cloning in baculovirus transfer vector. Twelve overlapping single stranded oligonucleotides, each 125–145 nucleotides in length and spanning the entire synthetic gene, are synthesized and the vaccine antigen gene assembled.

The order of different epitopes is chosen such that the final protein has: 1) a random balance of B- and T-cell epitopes; and 2) an overall hydrophilic structure and water solubility. The vaccine antigen gene is ligated into a transfer vector, preferably a baculovirus transfer vector, such as pBacPAK8, and the recombinants are used to transform host cells such as *Escherichia coli* XL-Blue component cells. For example, lipofectin-mediated transfection and in vivo homologous recombination were used to introduce the vaccine antigen gene from pBacPAK8 into *Autographa californica* nuclear polyhedrosis virus (AcNPV, strain E2) at the polyhedrin locus of the genome.

The synthetic gene is cloned, and the recombinant virus containing CDC/NIIMALVAC-1 gene produced and grown in confluent monolayer cultures of an Sf21 insect cell line. The expressed recombinant protein is then purified, preferably using affinity chromatography techniques, and its purity and specificity determined by known methods. Alternatively, the synthetic gene may be employed as a DNA vaccine.

A variety of expression systems may be employed for expression of the recombinant protein. Such expression methods include, but are not limited to the following: bacterial expression systems, including those utilizing *E. coli* and *Bacillus subtilis*; vaccinia virus systems; yeast expression systems; cultured insect and mammalian cells; and other expression systems known to one of ordinary skill in the art.

Purification and Characterization of the Expressed Protein

The expressed protein contains epitopes from the sporozoite stage, liver stage, blood stage and sexual stage (also known as the gametocyte stage) of the malarial parasite *P. falciparum*, as well as a melittin signal peptide, a polyhistidine sequence and an amino acid sequence from tetanus toxoid. Although the antigens (epitopes) listed in Example 1 and Table 1 are the preferred antigens, it is to be understood that other antigens derived from these different stages in the life cycle of *P. falciparum* may be employed and are within the scope of the present invention. It is also to be understood that amino acid substitutions, as described elsewhere herein, may be made for amino acids in the peptide epitopes listed in Table 1, and are within the scope of the present invention. The order of the arrangement of these epitopes may be important in producing an efficacious recombinant protein for use as an antimalarial vaccine against *P. falciparum*. Various arrangements of these epitopes are considered within the scope of the present invention, provided that the arrangements generate an immune response in the recipient to epitopes derived from different stages in the life cycle of *P. falciparum*. A preferred order of these epitopes is presented in FIG. 1. The expressed protein, herein referred to as CDC/NIIMALVAC-1, is immunogenic when administered in combination with a carrier and adjuvants to mice and rabbits. Antibodies produced against the recombinant protein CDC/NIIMALVAC-1 recognize epitopes in the sporozoite stage, liver stage, blood stage and sexual stage of the malarial parasite *P. falciparum*.

Antibody Production

The protein is combined with a pharmaceutically acceptable carrier or vehicle to produce a pharmaceutical composition, and is administered to animals for the production of polyclonal antibodies. The preferred animals for antibody production are rabbits and mice. Other animals may be employed for immunization with the recombinant protein. Such animals include, but are not limited to the following; sheep, horses, pigs, donkeys, cows, monkeys and rodents, such as guinea pigs, and rats. Monoclonal antibodies can then be produced using hybridoma technology in accordance with methods well known to those skilled in the art, as taught by Mason et al. (Techniques in Immunocytochemistry, Vol. 2, Bullock & Petrusz eds., Academic Press, pp. 175–216, 1983). The antibodies are useful as research or diagnostic reagents or can be used for passive immunization. The pharmaceutical composition used for generation of antibodies may contain an adjuvant.

The antibodies useful as research or diagnostic reagents may be employed for detection of malarial infection in a biological sample, especially infection caused by *P. falciparum*. Such capability is useful for early detection of disease so that the vaccine may be administered to ameliorate disease progression. This capability is also useful for detecting the malarial parasite in the blood, especially blood collected for blood banks, so that malarial transmission through this mode is reduced or eliminated. Other biological samples which can be examined for infection are samples of human and animal livers, and also mosquitoes. Detection may be achieved through the use of ELISA, radioimmunoassay or other assays or methods as commonly known to one of ordinary skill in the art.

The CDC/NIIMALVAC-1 protein may be labeled through commonly known isotopic and non-isotopic methods, including but not limited to the following: radiolabeling, biotin-avidin, fluorescent molecules, chemiluminescent molecules and systems, ferritin, colloidal gold, and other methods known in the art of labeling proteins. The anti-CDC/NIIMALVAC-1 antibodies may be used in combination with labeled CDC/NIIMALVAC-1 protein to detect epitopes in *P. falciparum*.

The anti-CDC/NIIMALVAC-1 antibodies may also be administered directly to humans and animals in a passive immunization paradigm to confer immunity in the recipient to malaria.

Method of Administration

The protein is combined with a pharmaceutically acceptable carrier or vehicle for administration as a vaccine to humans or animals. The terms "pharmaceutically acceptable carrier" or "pharmaceutically acceptable vehicle" are used herein to mean any liquid including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The vaccine formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The vaccine may be administered through different routes, such as oral, including buccal and sublingual, rectal, parenteral, aerosol, nasal, intramuscular, subcutaneous, intradermal, and topical. The vaccine may be administered in different forms, including but not limited to solutions, emulsions and suspensions, microspheres, particles, microparticles, nanoparticles, and liposomes. It is expected that from about 1 to 5 dosages may be required per immunization regimen. Initial injections may range from about 1 µg to 1 mg, with a preferred range of about 10 µg to 800 µg, and a more preferred range of from approximately 25 µg to 500 µg. Booster injections may range from 1 µg to 1 mg, with a preferred range of approximately 10 µg to 750 µg, and a more preferred range of about 50 µg to 500 µg.

The volume of administration will vary depending on the route of administration. Intramuscular injections may range from about 0.1 ml to 1.0 ml.

The vaccine may be stored at temperatures of from about 4° C. to −100° C. The vaccine may also be stored in a lyophilized state at different temperatures including room temperature. The vaccine may be sterilized through conventional means known to one of ordinary skill in the art. Such means include, but are not limited to filtration, radiation and heat. The vaccine may also be combined with bacteriostatic agents, such as thimerosal, to inhibit bacterial growth.

Vacciniation Schedule

The vaccine of the present invention may be administered to humans, especially individuals traveling to regions where malaria is present, and also to inhabitants of those regions. The optimal time for administration of the vaccine is about one to three months before the initial infection. However, the vaccine may also be administered after initial infection to ameliorate disease progression, or after initial infection to treat the disease.

Adjuvants

A variety of adjuvants known to one of ordinary skill in the art may be administered in conjunction with the protein in the vaccine composition. Such adjuvants include, but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; CpG oligonucleotide motifs and combinations of CpG oligonucleotide motifs; trehalose; bacterial extracts, including mycobacterial extracts; detoxified endotoxins; membrane lipids; or combinations thereof.

It will be appreciated that other embodiments and uses will be apparent to those skilled in the art and that the invention is not limited to these specific illustrative examples.

EXAMPLE 1

Development, Synthesis and Cloning of the CDC/NIIMALVAC-1 Gene

A recombinant multivalent and multistage vaccine against *P. falciparum* was designed to contain the secretory melittin signal peptide sequence, six histidine (His) residues for purification of the protein, one tetanus toxoid universal T-helper epitope, and 21 immunogenic peptide epitopes (12 B-cell epitopes and 9 T-cell epitopes) from the CSP, Pfg27, SSP-2, LSA-1, MSP-1, MSP-2, AMA-1, EBA-175, and RAP-1 vaccine antigens (see Table 1 and SEQ ID NOS:1–26). These malarial peptide epitopes were obtained from different stages of the life cycle of *P. falciparum* including the following stages: the sporozoite stage (CSP and SSP-2); liver stage (LSA-1); blood stage (MSP-1, MSP-2, AMA-1, EBA-175, and RAP-1); and sexual stage (Pfg27). The peptide epitopes of the CSP, LSA-1, MSP-1, AMA-1, and RAP-1 were identified through vaccine-related field studies in western Kenya, where the genetic diversity of candidate vaccine antigen genes and the characteristics of naturally acquired protective immunity against malaria were being investigated. The epitopes for the Pfg27, MSP-2, EBA-175, and SSP-2 were identified as involved in conferring protection. The synthetic gene (SEQ ID NO:1) encoding for the recombinant protein was assembled, cloned, and expressed in a baculovirus system. The recombinant gene encoded for a recombinant protein referred to herein as CDC/NIIMALVAC-1 having the sequence of SEQ ID NO:2.

A schematic map shown in FIG. 1 provides the locations of epitopes in CDC/NIIMALVAC-1 indicated by the codes corresponding to the codes in Table 1. The rationale of the arrangement of the immune epitopes reflects a random balance of position of B cell and T cell epitopes. Corresponding nucleotide sequences for the melittin signal peptide sequence, the six histidine residues and the epitopes from *P. falciparum* were constructed. The nucleotides shown adjacent to melittin and adjacent to P 599 in FIG. 1 are start and stop codons. Restriction enzyme sites BamHI and NotI were designed at the flanking end to facilitate cloning in baculovirus transfer vector. Twelve overlapping single stranded oligonucleotides, each 125–145 nucleotides in length and spanning the entire synthetic gene, were synthesized, and the gene encoding for the vaccine antigen was assembled.

The vaccine antigen gene was ligated into a baculovirus transfer vector, pBacPAK8, and the recombinants were used to transform *Escherichia coli* XL-Blue component cells. Lipofectin-mediated transfection and in vivo homologous recombination were used to introduce vaccine antigen gene from pBacPAK8 into *Autographa californica* nuclear polyhedrosis virus (AcNPV, strain E2) at the polyhedrin locus of the genome.

The strategy for constructing the gene encoding for CDC/NIIMALVAC-1 described in this example is shown in FIG. 2. Twelve long overlapping single-strand oligonucleotides, spanning the full length of gene, were synthesized and assembled through a three step PCR to generate a 1053 base pair gene. The PCR cycles used in each step are indicated in FIG. 2.

TABLE 1

Epitope location, amino acid sequences and epitope-specific antibody responses to CDC/NIIMALVAC-1[1]

| Antigens[2] | Epitope codes[2] | Sequences and SEQ ID Nos. | Stage[3] | Epitopes | Epitope-specific antibody response in rabbit[4] |
|---|---|---|---|---|---|
| Melittin signal peptide | Melittin | MKFLVNVALVFMV VYISYIYAD SEQ ID NO:25 | n.a.[5] | n.a. | n.a. |
| 6X His | 6X His | HHHHHH SEQ ID NO:26 | n.a. | n.a. | n.a. |
| CSP | P592 | KHKKLKQPGDGNP SEQ ID NO:5 | S | B | Neg |
| SSP-2 | P547 | WSPCSVTCG SEQ ID NO:8 | S | B | Neg |
| CSP | P593 | KPKDELDYENDIEK KICKMEKCS SEQ ID NO:6 | S | CTL | High |
| CSP | P594 | DIEKKICKMEKCSS VFNVVNS SEQ ID NO:7 | S | CS. T3 | Medium |
| MSP-1 | P597 | NSGCFRHLDEREEC KCLL SEQ ID NO:11 | B | B | Low |

TABLE 1-continued

Epitope location, amino acid sequences and epitope-specific antibody responses to CDC/NIIMALVAC-1[1]

| Antigens[2] | Epitope codes[2] | Sequences and SEQ ID Nos. | Stage[3] | Epitopes | Epitope-specific antibody response in rabbit[4] |
|---|---|---|---|---|---|
| MSP-1 | P598 | EDSGSNGKKITCEC TKPDS SEQ ID NO:12 | B | B | Neg |
| LSA-1 | P595 | KPIVQYDNF SEQ ID NO:9 | L | CTL | Medium |
| CSP | P519 | NANPNANPNANP SEQ ID NO:4 | S | B | High |
| AMA-1 | P600 | DGNCEDIPHVNEFS AIDL SEQ ID NO:16 | B | B | High |
| AMA-1 | P601 | GNAEKYDKMDEPQ HYGKS SEQ ID NO:17 | B | B | Medium |
| RAP-1 | P545 | LTPLEELY SEQ ID NO:21 | B | B | Medium |
| LSA-1 | P596 | KPNDKSLY SEQ ID NO:10 | L | CTL | Neg |
| P2, TT tetanus toxoid | P589 | QYIKANSKFIGITEL SEQ ID NO:24 | tetanus toxoid | T | Neg |
| MSP-2 | P543 | SNTFINNA SEQ ID NO:14 | B | B | Neg |
| MSP-2 | P544 | GQHGHMHG SEQ ID NO:15 | B | B | Neg |
| EBA-175 | P546 | NEREDERTLTKEYE DIVLK SEQ ID NO:20 | B | B | Low |
| AMA-1 | P603 | EFTYMINFGRGQNY WEHPYQKS SEQ ID NO:19 | B | T | Low |
| AMA-1 | P602 | DQPKQYEQHLTDYE KIKEG SEQ ID NO:18 | B | T | Low |
| Pfg27 | P591 | KPLDKFGNIYDYHY EH SEQ ID NO:3 | G | B | Low |
| RAP-1 | P604 | SSPSSTKSSPSNVKS AS SEQ ID NO:22 | B | T | Low |
| RAP-1 | P605 | LATRLMKKFKAEIR DFF SEQ ID NO:23 | B | T | Neg |
| MSP-1 | P599 | GISYYEKVLAKYKD DLE SEQ ID NO:13 | G | T | Neg |

[1]Location of immune epitopes in CDC/NIIMALVAC-1 is presented in the first column and indicated by the codes. A melittin signal peptide sequence and 6 histidine residues were incorporated at N-terminus.
[2]Abbreviations: CSP, circumsporozoite protein; SSP-2, sporozoite surface protein-2; LSA-1, liver stage antigen-1; MSP-1, merozoite surface protein-1; MSP-2, merozoite surface protein-2; AMA-1, apical membrane antigen-1; EBA-175, erythrocyte binding antigen-175; RAP-1, rhoptry associated protein-1; Pfg27, gametocyte 27 kDa antigen.
[3]In the column entitled "Stage", B represents Blood stage, L represents Liver stage, S represents Sporozoite stage, G represents gametocyte stage
[4]For epitope-specific antibody response, titers were determined based on the highest dilution of the samples which generate an optical density (OD) greater than the cutoff value (mean plus 3 standard deviations of preimmunization sera). ODs lower than cutoff at 1:50 dilution were considered a negative response. High response: titers are higher than 1:10,000; medium response: titers are 1:1,000–1:10,000; and low response: titers are 1:50–1:1,000.
[5]n.a. not applicable EXAMPLE 2
Expression of the Recombinant Protein in a Baculovirus System and Purification of the Protein Antigen The synthetic gene described in Example 1 was cloned and the recombinant virus containing the CDC/NIIMALVAC-1 gene was produced and grown in confluent monolayer cultures of Sf21 insect cell line, as described by Chatterjee, U. et al., (1996) *Gene* 171:209–213. The synthetic gene is approximately 1053 bp as determined on an agarose gel with corresponding DNA standards run in another lane.

The baculovirus-expressed, recombinant protein was purified from Sf21 cells at 72 hours postinfection using TALON metal affinity resin according to the manufacturer's instructions (Clonetech, Palo Alto, Calif.). The purity and specificity of the expressed recombinant protein were determined by sodium dodecyl sulfate polyacrylamide gel electrophoresis (SDS-PAGE) and Western blot analysis. The results show that expression of the synthetic gene in the baculovirus expression vector system produced a 42 kD protein referred to herein as CDC/NIIMALVAC-1.

EXAMPLE 3
Immunization of Rabbits Against the Expressed Protein and Demonstration of Immunoreactivity against Different Stages in the Life Cycle of *P. falciparum*

As described in Example 2, the baculovirus-expressed recombinant protein was purified from cell pellets harvested 72 hours after infection. The expressed protein CDC/NIIMALVAC-1 was purified on nickel affinity column to bind the polyhistidine residues near the N-terminus of the protein using TALON metal affinity resin according to manufacturer's instructions. The purity and specificity of protein was determined by sodium dodecyl sulfate polyacrylamide gel electrophoresis as described in Example 2. The isolated protein was characterized, using chromatographic techniques, as approximately 42 kD in size.

Six to eight week old mice were immunized intraperitoneally with 50 μg per dose of purified CDC/NIIMALVAC-1 protein in Freund's complete adjuvant. Booster immunizations of mice were 25 μg per dose of purified CDC/NIIMALVAC-1 protein in Freund's incomplete adjuvant. A total of 4 immunizations were given to each mouse at 3-week intervals (i.e., at weeks 0, 3, 6, and 9), blood was removed and sera were collected 7 to 10 days after each immunization until weeks 33–51. Sera were stored at −20° C. The sera from mice were, used in the antibody and immunofluorescence (IFA) assays.

Four-month-old female New Zealand white rabbits (Jackson Laboratory, Bar Harbor, Me.) were immunized intramuscularly with 100 μg per dose of purified CDC/NIIMALVAC-1 protein in vehicle. One rabbit was immunized with the protein in Freund's adjuvant (rabbit 787). Another rabbit was immunized with the protein in a potentially human-usable adjuvant, specifically the nonionic block copolymer P1005in water-in-oil emulsion (rabbit 789). Another rabbit was immunized with the protein in the human usable adjuvant, aluminum hydroxide (rabbit 1015). A total of 4 immunizations were given to each rabbit at 3-week intervals (i.e., at weeks 0, 3, 6, and 9), blood was removed and sera were collected 7 to 10 days after each immunization until weeks 33–51. Sera were stored at −20° C. The sera from rabbits were used in the antibody and IFA assays.

Sera collected from the blood of each rabbit during weeks 10 to 16 were pooled and total IgGs were purified using ammonium sulfate (Sigma Chemical Co., St. Louis, Mo.) precipitation followed by DEAE (Pierce, Rockford, Ill.) batch purification according to known methods as taught by Hollingdale, M. R. et al., (1984) *J. Immunol.* 132, 909–913. Following dialysis against PBS, the purified antibodies were used for immunoelectron microscopy, antibody affinity testing, and in an in vitro protection assay Serum antibody titers against the vaccine antigen and individual peptide epitopes were quantitated by ELISA. Microtiter plates were coated with the vaccine antigen or peptides in borate buffer solution (BBS) overnight at 4° C. and then blocked with BBS containing 5% nonfat lyophilized milk. The plates were washed four times with sodium phosphate-buffered saline (PBS, pH 7.4) containing 0.5 M NaCl, 0.5% bovine serum albumin, 0.0005% Tween 20, and 0.05% thimerosal (PBS-T). The rabbit sera were diluted serially in PBS-T containing 1.5% nonfat milk, added into microtiter plates, and incubated at room temperature for 1 hour. The unbound antibodies were removed by four washes with PBS-T. Bound antibodies were detected with peroxidase-conjugated goat anti-rabbit antibodies. The secondary antibody was allowed to bind for 1 hour, the wells were washed with PBS-T, 100 $\mu$l of 3,3',5,5'-tetramethylbenzidine was added, and 10 minutes later the reaction was stopped with 1M phosphoric acid. The plates were read at an absorbance of 450 nm. Responses against sporozoites, asexual blood-stage parasites, and gametocytes were determined by indirect immunofluorescence (IFA). All immunized rabbits had high and comparable IFA titers against sporozoites (1:3,200). IFA titers against infected erythrocytes were in the range of 1:50–1:400, with the highest titers observed in the rabbit receiving copolymer as adjuvant. The reactivity with gametocytes showed IFA titers of 1:25 to 1:100.

The CDC/NIIMALVAC-1 protein was found to be immunogenic as confirmed by its ability to elicit immune responses against both CDC/NIIMALVAC-1 and different stages in the life cycle of the P. falciparum parasite. Antibody was purified from the rabbit immunized with CDC/NIIMALVAC-1 in copolymer adjuvant.

The immunoreactivity of this purified rabbit antiserum against antigens present in the different stages of the life cycle of the malarial parasite, P. falciparum, was evaluated using ultrastructural immunocytochemistry. To study ultrastructural localization of antibody reactivities with various stages of P. falciparum, sporozoite, exoerythrocytic (EE)-infected hepatocyte, gametocyte stage III-IV, and asexual blood stage parasites were chosen for immunoelectron microscopy. Briefly, sections were incubated for 24 hours at 4° C. with antibody diluted 1:800 for determination of reactivity with sporozoites, or with antibody diluted 1:200 for determination of reactivities with other stages of parasites. This step was followed by 1 hour incubation at 25° C. with gold-labeled, goat anti-rabbit IgG antibody. Method specificity was confirmed by incubating control sections with preimmune rabbit serum instead of the primary antibody, with the colloidal gold probe, or with colloidal gold alone. Immunoreactivities of antibodies with parasites were examined in a Zeiss CEM902 electron microscope as taught by Aikawa, M. & Atkinsen, C. T. (1990) Adv. Parasitol. 29, 151–214.

Immunoelectron micrographs of different stages in the life cycle of the P. falciparum parasite demonstrated that the rabbit antiserum from rabbit 789, which received copolymer as adjuvant, contained antibodies which were immunoreactive to the sporozoite stage, blood stage, gametocyte stage III-IV, and asexual blood stage. Gold particles were found on the surface and in the cytoplasm of the sporozoite, in the parasitophorous vacuole membrane (PVM) and cytoplasm of blood stage, in the cytoplasm in the gametocyte stage III-IV, in rhoptry and surface of merozoite of the blood stage and in the cytoplasm of trophozoite of the blood stage. There was no observed immunoreactivity against these stages using purified IgG from a normal control rabbit instead of the purified immune serum from the immunized rabbit.

Immunogenicity of the Multicomponent P. falciparum Vaccine

Figure 3:
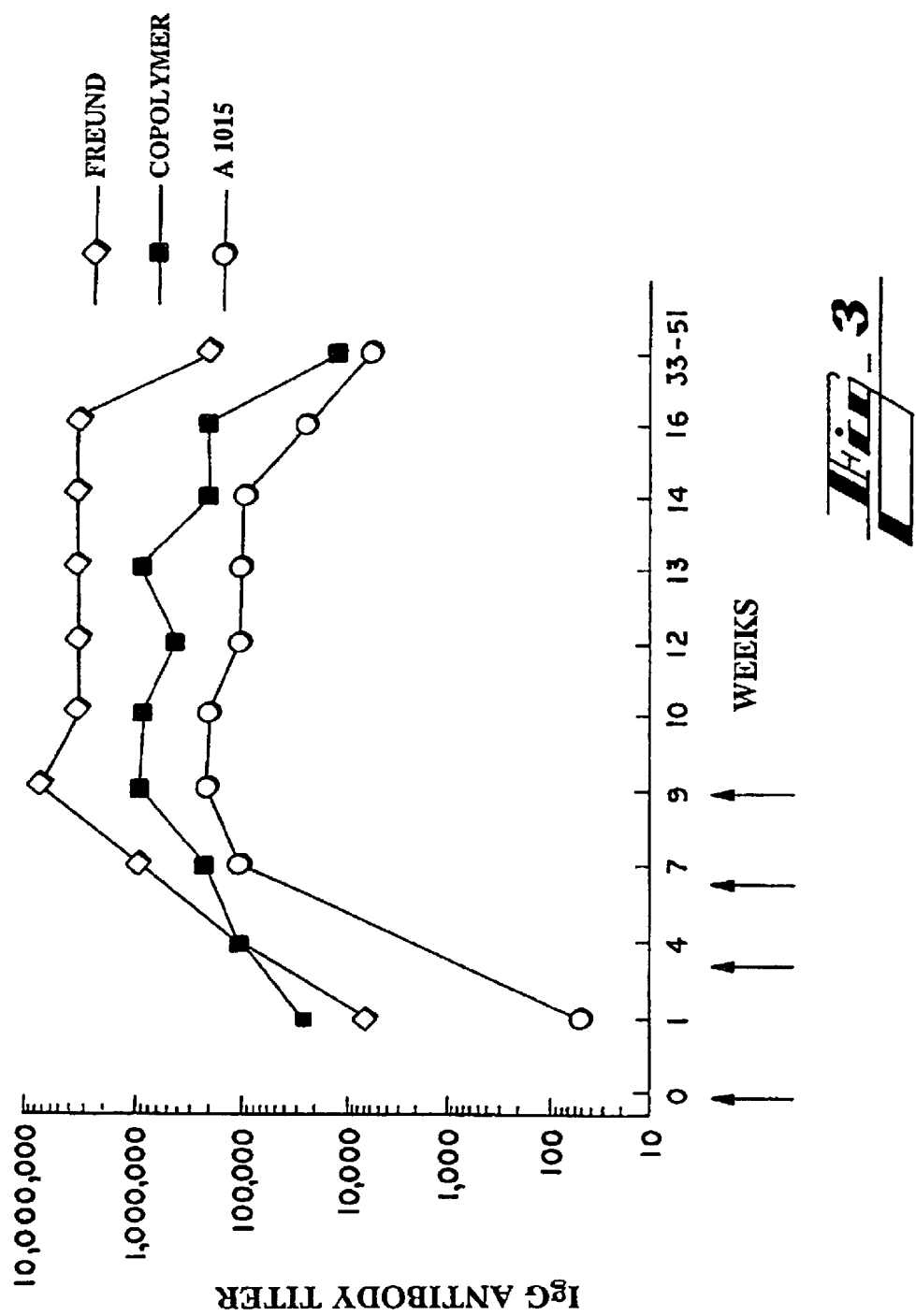
FIG. 3 is a graph showing antibody responses in sera as measured by ELISA. Rabbits were immunized with purified CDC/NIIMALVAC-1 using different adjuvant formulations at weeks 0, 3, 6, 9 as indicated by arrows. Antibody responses to CDC/NIIMALVAC-1 in the sera from rabbits receiving Freund's adjuvant (open diamond), copolymer (solid square), and aluminum hydroxide (open circle) as adjuvant were measured. Titers were determined based on the highest dilution of the samples that generated an optical density (OD) greater than the cutoff value (mean plus three standard deviations of pre-immunization sera). ODs lower than the cutoff value at 1:50 dilution were considered negative responses.

Antibody titers against the vaccine antigen CDC/NIIMALVAC-1 and peptides complementary to 22 immune epitopes (Table 1) were measured by ELISA after each immunization until week 51 for rabbit 787 (Freund's adjuvant), week 39 for rabbit 789 (copolymer adjuvant), and week 33 for rabbit 1015 (alum adjuvant). FIG. 3 shows that the vaccine antigen induced high titer and prolonged antibody responses against the vaccine in rabbits immunized with different adjuvants (1/3,276,800 titer for rabbit 787, 1/819,200 titer for rabbit 789, and 1/204,800 titer for rabbit 1015, after the fourth immunization). Overall, the rabbit receiving Freund's adjuvant had higher antibody levels to the vaccine antigen compared to those receiving copolymer or alum adjuvants. The antibody responses reached maximal levels after the fourth immunization, remained at high levels until weeks 14 to 16, and then decreased 10- to 15-fold between weeks 33 to 51.

Analysis of epitope-specific antibody responses by ELISA showed that the antibodies recognized both B-cell (7 out of 12) and T-cell (6 out of 10) epitopes in this vaccine. Among the epitope-specific antibody responses, antibody levels against B-cell epitopes of CSP (P519), AMA-1 (P600), and CTL epitope of CSP (P593), were significantly higher than antibody levels to other epitopes. Like antibody responses to the whole vaccine antigen, the antibody titer against these epitopes was also higher in rabbits receiving vaccine with Freund's adjuvant and copolymer adjuvant than those receiving vaccine with alum as adjuvant. Medium-to-low antibody responses to other epitopes were observed. Medium-level antibody responses were observed against the B-cell epitopes of AMA-1 and RAP-1 (P601 and P545), and T-cell epitopes of CSP and LSA-1 (P594 and P595). Low-level antibody responses were detected against B-cell epitopes of EBA-175, MSP-1 and Pfg27 (P546, P597, and P591), and T-cell epitopes of AMA-1 and RAP-1 (P602, P603 and P604).

Figure 4:
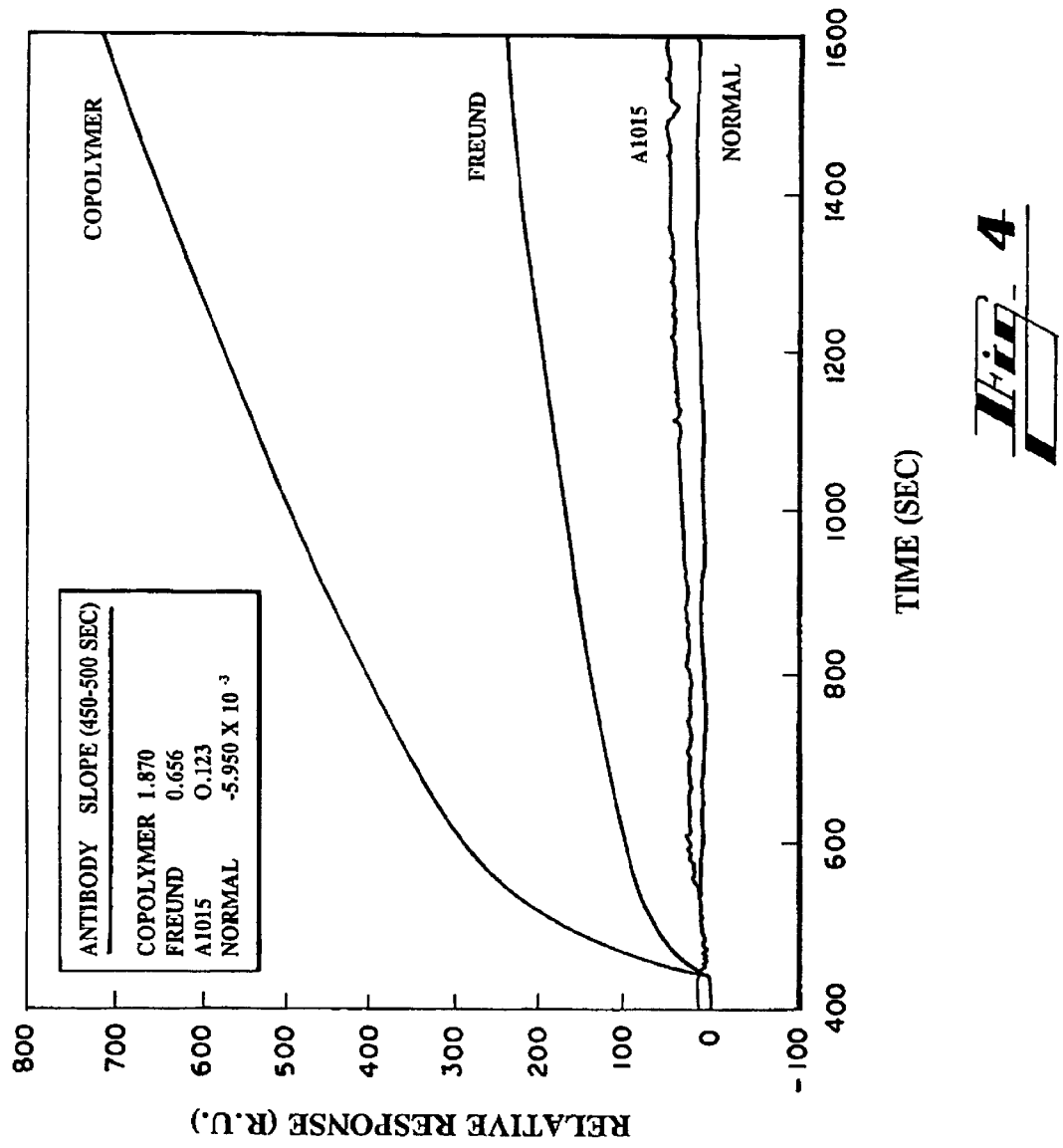
FIG. 4 is a graph showing binding of IgGs. Purified antibodies at concentration of 50 $\mu$g/ml were presented at 5 $\mu$l/min to a BIAcore sensor cell loaded with CDC/NIIMALVAC-1 protein. A chart on top left represents initial velocities of association (450–500 sec).

The binding affinities of the vaccine-elicited antibodies to the vaccine antigen itself were investigated in a Biacore assay employing a surface-plasmon resonance detector (Biacore, Inc., Piscataway, N.J.). Purified vaccine antigen was covalently immobilized in a "C1" (short-chain carboxymethyl-dextran) sensor cell by standard carbodiimide/N-hydroxysuccinimide methods. Mobile-phase analyte consisted of purified IgG preparations diluted to 50 $\mu$g of protein per ml in 10 mM HEPES buffer, pH 7.4, plus 150 mM NaCl. After establishing a stable baseline signal with buffer, the association reaction was initiated by switching to the analyte stream, and the resonance signal followed in time, as taught by Wohlhueter, R. M. et al., (1994) J. Immunol. 153, 181–189. A flow rate of 5 $\mu$l/min was used throughout. Association rate curves observed with different IgG preparations were adjusted to a common baseline and superimposed. Initial velocities of association of the high-affinity components were estimated by measuring the initial linear slopes of the curves (e.g., in the interval of 430 to 500 seconds on the abscissa of FIG. 4). Antigen-antibody binding showed multiple kinetic components distinguishable into fast (450–500 seconds) and slow (800–1400 seconds) components (FIG. 4). Quantitatively, total IgG from the rabbit (#789) immunized in the presence of copolymer adjuvant contained much higher levels of high affinity antibodies. This conclusion was also supported by the biological analysis described below.

EXAMPLE 4

Use of Growth Inhibition Assays (GIA) and Antibody Dependent Cellular Inhibition Assays (ADCI) for Determining Growth Inhibitory Effects of Purified Antibodies Antibodies were purified from rabbits immunized with the CDC/NIIMALVAC-1 protein in Freund's adjuvant (R-Freund's), in copolymer adjuvant (R-copolymer), and in alum adjuvant (R-alum-1 and R-alum-2), respectively. The results of in vitro experiments, performed to test the protective effects of antibodies with (antibody dependent cellular inhibition, ADCI) or without human monocytes (growth inhibition assay, GIA), showed that the antibodies against CDC/NIIMALVAC-1 inhibited parasite growth (Table 2B). The inhibitory effects were directly related to the concentration of antibodies (Table 2B).

Inhibition of sporozoite invasion (ISI) assays were conducted to determine the inhibitory effects of antibodies as previously described by Hollingdale, M. R. et al., (1984) *J. Immunol.* 132, 909–913. Briefly, the purified antibodies were added at two different final concentrations (25 and 50 µg/ml) into the HepG2-A16 hepatoma cells, and then about 30,000 *P. falciparum* sporozoites were added. The cells were incubated at 37° C. in 5% $CO_2$ for 3 hours, rinsed two times with phosphate-buffered saline (PBS), and fixed with methanol. Sporozoites that had entered hepatoma cells were visualized by immunocytochemical staining with a monoclonal antibody to *P. falciparum* sporozoites (NSF1), peroxidase-conjugated, goat anti-mouse immunoglobulin and the substrate 3,3-diaminobenzidine. All cultures were done in triplicate and the numbers of sporozoites that had invaded the hepatoma cells were determined by light microscopy.

Antibody dependent cellular inhibition (ADCI) assays were carried out using described methods (Bouharoun-Tayoun, H. et al., (1995) *J. Exp. Med.* 182, 409–418; Shi, Y. P. et al., (1999) *Am. J. Trop. Med. Hyg.* 60(1), 135–141). Briefly, the purified antibodies were added at three different final concentrations (12.5, 25, and 50 µg/ml) into FC27 strain blood-stage parasite cultures (0.3% parasitemia with 60% schizonts, and 1% hematocrit), along with 80,000 rhIFN-gamma (100 ng/ml)-activated human monocytes. The cell cultures were incubated at 37° C. in a mixed gas containing 5% $O_2$, 5% $CO_2$, and 90% $N_2$ for 72 hours, with medium and antibody replacement every 24 hours. Parasites were stained with the vital dye hydroethidine (HE) and parasitemias were determined by a flow cytometry-based parasite enumerating procedure using FACScan. Transmission-blocking assays were performed by membrane feeding assays as taught by Wizel B. & Kumar, N. (1991) *Proc. Natl. Acad. Sci. USA* 88, 9533–9536. In this assay, *P. falciparum* (3D7) gametocytes were used to infect *An. stephensi* mosquitoes. Various IgG preparations were tested at the final concentration of 125 to 500 µg/ml.

Determination of in vitro Antiparasite Activity of Vaccine-elicited Antibodies

Antibodies from rabbits immunized with the vaccine in different adjuvants strongly inhibited sporozoite invasion of HepG2-A16 cells (Table 2A). Antibodies from the rabbit which received the vaccine in block copolymer adjuvant almost completely inhibited sporozoite invasion (98% inhibition) at an antibody concentration of 50 µg/ml. This level of inhibition was comparable with the inhibition observed using a positive monoclonal antibody control. Antibodies elicited against the vaccine in the presence of alum or Freund's adjuvants also inhibited invasion of sporozoites, although at lower levels. At 25 µg/ml, antibody-mediated inhibition was again most prominent in the case of antibodies from rabbits vaccinated with recombinant protein plus block copolymer adjuvant.

ADCI experiments showed that the vaccine-elicited antibodies had significant inhibitory effects on in vitro growth of blood-stage parasites in the presence of monocytes. No growth inhibitory effects in the absence of monocytes were observed. The most striking ADCI activity was mediated by antibodies from the rabbit which received the vaccine copolymer formulation (73% inhibition); lower activity was observed in those animals receiving vaccination in Freund's adjuvant (70%), and alum adjuvant (67%) (Table 2B). A concentration-dependent, antibody inhibition of growth was observed in the ADCI assay (Table 2B). As compared with the ADCI activity with the rabbit antivaccine antibodies, the activity of purified IgGs from Kenyan adults, who were clinically immune to malaria, was much lower (between 15%–29%). As compared with the sporozoite and blood-stage inhibitory activities, the results of transmission blocking assays did not reveal any significant inhibition.

EXAMPLE 5

Test of Immunogenicity and Protective Efficacy of the Multivalent Vaccine in a Monkey Model System Monkeys received about 100 µg of the vaccine described in Example 3 per animal for initial immunization and approximately 200 µg per animal for booster injection. Animals were immunized with vaccine alone, and also in the presence of one of the following different adjuvants: alum; copolymer P1005 in saline; copolymer P1005 in water-in-oil; QS21 (Acquila Biopharmaceuticals, Boston, Mass.); Freund's complete adjuvant followed by Freund's incomplete adjuvant; and SBAS2 (Smith-Kline-Beechum, Belgium). The non-immunized group served as a control. Seven A. nancymai monkeys were assigned per treatment group except for the control group of 6 animals (n=55). After 4 immunizations, animals are challenged with live parasites and the course of parasitemia is monitored in immunized and non-immunized animals using techniques known to one of ordinary skill in the art. Blood samples are collected periodically throughout the trial to

TABLE 2

Evaluation of in vitro anti-parasitic activities of CDC/NIIMAL VAC-1 elicited antibodies A: Inhibition of sporozoite invasion (ISI)

| | Antibody concentrations (ug/ml) | | | |
|---|---|---|---|---|
| | 50 | | 25 | |
| Antibodies | Invasion number[1] | % inhibition[2] | Invasion number[1] | % inhibition[2] |
| Preimmune[3] | 131 (10) | 0 | 112 (7) | 0 |
| Freund | 19 (3) | 85 | 29 (3) | 74 |
| Copolymer | 3 (2) | 98 | 10 (3) | 91 |

TABLE 2-continued

Evaluation of in vitro anti-parasitic activities of CDC/NIIMAL VAC-1 elicited antibodies

| | | | | |
|---|---|---|---|---|
| Alum 1015 | 15 (2) | 89 | 23 (4) | 79 |
| Positive control[4] | ND | ND | 2 (2) | 98 |

[1]Mean number of *P. falciparum* sporozoites that entered triplicate cell culture with standard deviation (SD) given in parenthesis.
[2]% inhibition expressed relative to pre-immune control culture (0%), which was calculated as follow: 100 × [1 − (mean number of invaded sporozoites in test culture/mean number of invaded sporozoites in control culture)].
[3]Preimmune, antibodies purified from preimmune rabbits used as negative control; Freund, antibodies purified from rabbit receiving Freund's as adjuvant; Copolymer, antibodies purified from rabbit receiving non-ionic block copolymer P1005 as adjuvant; Alum 1015, antibodies purified from rabbit receiving aluminum hydroxide as adjuvant.
[4]Monoclonal antibody against sporozoites (NFS1) used as positive control.
ND: not done.

B: Growth inhibition of the blood-stage parasite in the presence of monocytes (ADCI)

| | Antibody concentrations (ug/ml) | | | | | |
|---|---|---|---|---|---|---|
| | 50 | | | 25 | | |
| | Parasitemia | | % | Parasitemia | | % |
| Antibodies | No monocyte[1] | Monocyte[1] | inhibition[2] | No monocyte[1] | Monocyte[1] | inhibition[2] |
| Preimmune[3] | 2.56 (0.07) | 1.04 (0.1) | 0 | 3.39 (0.09) | 2.25 (0.065) | 0 |
| Freund | 3.33 (0.07) | 0.65 (0.025) | 70 | 3.49 (0.04) | 1.77 (0.125) | 23 |
| Copolymer | 2.85 (0.09) | 0.50 (0.025) | 73 | 3.10 (0.12) | 1.43 (0.11) | 30 |
| Alum 1015 | 2.87 (0.14) | 0.63 (0.11) | 67 | 3.33 (0.05) | 1.10 (0.05) | 50 |
| Positive control[4] | 3.17 (0.1) | 1.17 (0.035) | 29 | | ND | |

| | Antibody concentrations (ug/ml) | | |
|---|---|---|---|
| | 12.5 | | |
| | Parasitemia | | |
| Antibodies | No monocyte[1] | Monocyte[1] | % inhibition[2] |
| Preimmune[3] | 3.75 (0.13) | 2.40 (0.105) | 0 |
| Freund | 3.56 (0.025) | 2.19 (0.095) | 7 |
| Copolymer | 3.46 (0.01) | 1.68 (0.06) | 26 |
| Alum 1015 | 3.65 (0.125) | 1.40 (0.17) | 42 |
| Positive control[4] | | ND | |

[1]Mean of parasitemias in duplicate cell culture with standard deviation (SD) given in parenthesis.
[2]% inhibition expressed relative to preimmune control culture (0%) and taking into account the possible inhibition induced by monocyte and antibody alone, which was calculated as follows: 100 × [1 − ((mean parasitemia with test IgG and monocyte/mean parasitemia with test IgG and without monocyte)/(mean parasitemia with control IgG and monocyte/mean parasitemia with control IgG and without monocyte))].
[3]Preimmune, antibodies purified from preimmune rabbits used as negative control; Freund, antibodies purified from rabbit receiving Freund's as adjuvant; Copolymer, antibodies purified from rabbit receiving non-ionic block copolymer P1005 as adjuvant; Alum 1015, antibodies purified from rabbit receiving aluminum hydroxide as adjuvant.
[4]Purified antibody from Kenyan immune adult (1 mg/ml) used as positive control.
ND: not done evaluate humoral and cellular immune responses to CDC/NIIMALVAC-1 and to various peptides contained within CDC/NIIMALVAC-1.

EXAMPLE 6

Determination of Immunogenicity of CDC/NIIMALVAC-1 in Inbred Mice

Six- to eight-week old female, inbred strains of mice, C57BL/6 ($H-2^b$), B10.BR ($H-2^k$), and B10.D2 ($H-2^d$), were immunized subcutaneously with about 10 μg of purified CDC/NIIMALVAC-1 with alum adjuvant, or with a non-ionic copolymer adjuvant P1005 in a water-in-oil emulsion. Control mice received only either adjuvant. A booster dose (10 μg/mouse) was given 2 weeks after the primary immunization. Mice were bled at different time intervals, and cellular and humoral immune responses were determined according to published techniques (Lal, A. A., et al., (1996) *Infect. Immun.* 64, 1054–1059; Coligan, J. E., et al., Current protocols in immunology (1996), Vol. 1, pp. 2.1.2–2.1.6, pp. 3.12.1–3.1.4, pp. 6.8.1–6.8.3, and Vol. 2, pp. 7.10.1–7.10.6, National Institutes of Health, John Wiley & Sons, Inc.).

B10.BR mice, irrespective of the adjuvant used, generated highest antibody titers after two immunizations. In the C57BL/6 mice, copolymer adjuvant induced the highest antibody titer. B10.D2 mice were low responders, but the copolymer adjuvant induced higher antibody responses than alum (FIG. 5). These results demonstrate that antibody production against CDC/NIIMALVAC-1 is influenced by both mouse H-2 genetic background and the adjuvant used for immunization.

The best proliferative response was observed in B10.BR mice followed by C57BL/6 mice and B10.D2 mice. The stimulation index (SI), which is a measurement of proliferative responses, in the adjuvant control group of mice was less than 2, indicating that the vaccine-induced response is specific as taught by Lal, A. A. et al., (1996) Infect. Immun. 64, 1054–1059. The peak proliferative response was observed on day 21, and the response declined at the subsequent time points (Table 3). IFN-γ levels were specifically elevated in immunized mice when compared to adjuvant control mice (Table 4). This IFN-γ response, unlike the proliferative response, was similar in all three strains of mice.

EXAMPLE 7

Immunogenicity of CDC/NIIMALVAC-1 in Outbred Mice Using Different Adjuvant-Vaccine Formulations Outbred ICR mice were immunized subcutaneously with 10 µg of CDC/NIIMALVAC-1 (2 injections total) at two week intervals in the presence of CpG oligonucleotides, QS21, copolymer and alum adjuvants. Control mice were given adjuvant alone. Four days after the second immunization, spleens were collected from two

TABLE 3

Proliferative response to CDC/NIIMAL VAC-1 in immunized inbred mice

| Mice | Day of assay[1] | Alum control[2] | Alum + vaccine | Copolymer control | Copolymer + vaccine |
|---|---|---|---|---|---|
| C57BL/6 | 21 | 0.428 | 4.12 | NT[3] | 2 |
|  | 34 | 1.2 | 3.21 | 1.39 | 2.07 |
|  | 48 | 1.2 | 1.6 | 0.83 | 0.35 |
| B10.BR | 21 | 1.11 | 8 | 1.15 | 6.74 |
|  | 34 | 1.97 | 4.92 | 0.97 | 3.64 |
|  | 48 | 1.59 | 5.07 | 1.68 | 4.08 |
| B10.D2 | 21 | 0.29 | 1.2 | 0.59 | 3.4 |
|  | 34 | 1.02 | 1.98 | 1.09 | 1.9 |
|  | 48 | 0.66 | 3.33 | 0.32 | 2.24 |

[1] Indicates the time at which after first immunization the spleens were obtained for in vitro proliferative assay. Spleens from two immunized or control mice were pooled and proliferative assays were done as described in the specification.
[2] The value represents stimulation index. A stimulation index of >2 was considered a positive response.
[3] Not tested

TABLE 4

IFN-γ response to CDC/NIIMAL VAC-1 in immunized inbred mice

| Mice | Day of assay | Alum control | Alum + vaccine | Copolymer control | Copolymer + vaccine |
|---|---|---|---|---|---|
| C57BL/6 | 21 | 16 | 0.48 | 74 | 11 |
|  | 34 | 0 | 743 | 0 | 1641 |
|  | 48 | 247 | 1449 | 0 | 1413 |
| B10.BR | 21 | 4 | 0.13 | 295 | 65 |
|  | 34 | 168 | 2614 | 0 | 1745 |
|  | 48 | 9 | 967 | 0 | 1633 |
| B10.D2 | 21 | 14 | 10 | 0 | 0 |
|  | 34 | 318 | 925 | 0 | 1051 |
|  | 48 | 10 | 1320 | 0 | 2508 |

Spleens from two mice were pooled and cultured at $1 \times 10^6$ cell/well in 48 well plate. The cultures were stimulated with 1 µg/ml of CDC/NIIMALVAC-1 and supernatants were collected 48 hours later. The values are expressed as pg/ml of IFN-γ in the culture supernatant and these values are represented after the subtraction of background cytokine levels in unstimulated control cultures. immunized mice and one control mouse. The T cell responses to the vaccine and the synthetic peptides corresponding to the epitopes included in the vaccine were evaluated using the in vitro proliferative assay. The results are presented as stimulation index (SI). SI values of greater than 2 are considered positive. Total IgG antibody levels against the vaccine antigen in mice at day 45 and day 60 were determined using ELISA.

The mice immunized with the QS21 and the copolymer adjuvant-vaccine formulations displayed elevated total IgG antibody titers 2 weeks after the third immunization, and maintained high total IgG antibody titers 5 weeks after the third immunization. All mice immunized with different adjuvant-vaccine formulations were able to induce a strong proliferative response to CDC/NIIMALVAC-1. These proliferative responses, observed in an in vitro stimulation assay, were dependent on the antigen concentration. Among the four adjuvants, alum, CpG, and QS21-vaccine formulations induced a proliferative response to some of the individual epitopes (Pfg27, CSP, MSP-1, AMA-1, EBA-175 and RAP-1) (Table 5). Control mice immunized with adjuvant alone showed no antibody response or proliferative response to CDC/NIIMALVAC-1, indicating that the humoral and cellular immune responses are vaccine specific. These results indicate that the T cells of mice immunized with CDC/NIIMALVAC-1 recognize individual peptide epitopes derived from different stages in the life cycle of P. falciparum and contained within the vaccine. These data also suggest that the vaccine is effective in conferring protection to the different stages in the life cycle of P. falciparum.

EXAMPLE 8

Determination of Immune Responses to CDC/NIIMALVAC-1 in Individuals Naturally Exposed to Malaria Lymphocyte proliferation, cytokine, and antibody responses to CDC/NIIMALVAC-1 were tested in nonimmune children and clinically immune adults from western Kenya, a malaria holoendemic area. Finger prick samples of heparinized blood were used in this study. The serum samples were used in determining the antibody response against the vaccine antigen and/or peptides in the vaccine antigen using ELISA methodology. In the case of T-cell proliferation assays, peripheral blood mononuclear cells (PBMCs) from these individuals were used. The PBMCs were cultured in the presence of vaccine antigen, CDC/NIIMALVAC-1. The T-cell proliferation was measured quantitatively and the cell culture supernatant was used for measuring cytokine levels using published techniques (Lal, A. A., et al., (1996) Infect. Immun. 64, 1054–1059; Coligan, J. E., et al., Current protocols in immunology (1996), Vol. 1, pp. 2.1.2–2.1.6, pp. 3.12.1–3.1.4, pp. 6.8.1–6.8.3, and Vol. 2, pp. 7.10.1–7.10.6, National Institutes of Health, John Wiley & Sons, Inc.).

TABLE 5

Epitope-specific proliferative response in outbred mice immunized with different adjuvant-vaccine formulations

| Antigen | Stage | | Alum | V/Alum | V/Alum | CpG | V/CpG | V/CpG | QS21 | V/QS21 | V/QS21 | CoP | V/CoP | V/CoP |
|---|---|---|---|---|---|---|---|---|---|---|---|---|---|---|
| Pfg27 | Gametocyte | 591 | | xxxxx | | | | | | | | | | |
| CSP | Sporozoite | 519 | | | | | | | | | | | | |
| CSP | Sporozoite | 593 | | | | | xxxxx | | | | | | | |
| CSP | Sporozoite | 594 | | | | | | | | | | | | |
| SSP-2 | Sporozoite | 547 | | | | | | | | | | | | |
| LSA-1 | Liver Stage | 595 | | | | | | | | | | | | |
| LSA-1 | Liver Stage | 596 | | | | | | | | | | | | |
| MSP-1 | Blood Stage | 597 | | | | | xxxxx | | | | | | | |
| MSP-1 | Blood Stage | 598 | | | | | | | | | | | | |
| MSP-1 | Blood Stage | 599 | | | xxxxx | | | | | xxxxx | | | | |
| MSP-2 | Blood Stage | 543 | | | | | | | | | | | | |
| MSP-2 | Blood Stage | 544 | | | | | | | | | | | | |
| AMA-1 | Blood Stage | 600 | | | | | | | | | | | | |
| AMA-1 | Blood Stage | 601 | | | | | | | | | | | | |
| AMA-1 | Blood Stage | 602 | | xxxxx | | | | | | | | | | |
| AMA-1 | Blood Stage | 603 | | | | | | | | | | | | |
| EBA-175 | Blood Stage | 546 | | xxxxx | | | xxxxx | | | xxxxx | xxxxx | | | |
| RAP-1 | Blood Stage | 545 | | | | | xxxxx | | | | | | | |
| RAP-1 | Blood Stage | 604 | | | | | | | | | | | | |
| RAP-1 | Blood Stage | 605 | | xxxxx | | | xxxxx | | | | | | | |
| P2 | Tetanus Toxoid | 589 | | | | | | | | | | | | |

☐ : Negative response xxxxx : Positive response

PBMCs from 76 infants age less than 12 months, and 59 adults from western Kenya, were examined for proliferative responses to CDC/NIIMALVAC-1. The individuals with a stimulation index (SI) value greater than 2.5 were considered positive responders. The results showed no difference in the rate of positive responders and the SI levels between infants and adults. However, PBMCs from infants required much higher concentrations of CDC/NIIMALVAC-1 for in vitro stimulation compared to the PBMCs from clinically immune adults. Among 37 infant positive responders, 73% displayed a high proliferative response when using antigen concentrations between 0.5 and 1 µg/ml, whereas 19% required 2.5 to 5 µg/ml of antigen. In contrast, 79% of adult positive responders (n=28) required an antigen concentration of from about 0.001 to 0.1 µg/ml for in vitro stimulation. These results indicate that malaria-specific immune activation is much higher in adults than in infants in a malaria holoendemic area.

All patents, publications and abstracts cited above are incorporated herein by reference in their entirety.

It should be understood that the foregoing relates only to preferred embodiments of the present invention and that numerous modifications or alterations may be made therein without departing from the spirit and the scope of the present invention as defined in the following claims.

What is claimed is:

1. A single recombinant protein comprising peptides from two or more stages in a life cycle of *Plasmodium falciparum* wherein each peptide comprises an antigenic epitope comprising the amino acid sequence as forth as SEQ ID NO: 3, 4, 5, 6, 7, 8, 9, 10, 11, 12, 13, 14, 15, 16, 17, 18, 19, 20, 21, 22, 23, 24, or 25.

2. A recombinant protein comprising the amino acid sequence as set forth as SEQ ID NO: 2.

3. The protein of claim 1, further comprising a signal peptide, polyhistidine and T-cell helper epitope.

4. The protein of claim 1, wherein the stages are selected from sporozoite, liver, blood, and sexual stages of *Plasmodium falciparum* life cycle.

5. The protein of claim 4, comprising at least one antigenic epitope from each of the sporozoite, liver, blood and sexual stages of *Plasmodium falciparum* life cycle.

6. A protein composition comprising the recombinant protein of claim 1 in a pharmaceutically acceptable carrier.

7. The protein of claim 1, wherein each antigenic epitope consists of the amino acid sequence as set forth as SEQ ID Nos: 3, 4, 5, 6, 7, 8, 9, 10, 11, 12, 13, 14, 15, 16, 17, 18, 19, 20, 21, 22, 23, 24, or 25.

* * * * *

SEQUENCE LISTING

```
<160> NUMBER OF SEQ ID NOS: 26

<210> SEQ ID NO 1
<211> LENGTH: 1053
<212> TYPE: DNA
<213> ORGANISM: Artificial Sequence
<220> FEATURE:
<223> OTHER INFORMATION: Recombinant DNA/Protein
<221> NAME/KEY: CDS
<222> LOCATION: (1)..(1053)
<223> OTHER INFORMATION:
```

<400> SEQUENCE: 1

```
atg aaa ttc tta gtc aac gtt gcc ctt gtt ttt atg gtc gtg tac att      48
Met Lys Phe Leu Val Asn Val Ala Leu Val Phe Met Val Val Tyr Ile
 1               5                  10                  15 tct tac atc tat gcg gat cat cat cat cat cat aaa cat aaa aaa          96
Ser Tyr Ile Tyr Ala Asp His His His His His His Lys His Lys Lys
                20                  25                  30 tta aag caa cca ggg gat ggt aat cct tgg tcc cca tgt agt gta act     144
Leu Lys Gln Pro Gly Asp Gly Asn Pro Trp Ser Pro Cys Ser Val Thr
            35                  40                  45 tgt gga aaa cct aaa gac gaa tta gat tat gaa aat gat att gaa aaa     192
Cys Gly Lys Pro Lys Asp Glu Leu Asp Tyr Glu Asn Asp Ile Glu Lys
 50                  55                  60 aaa att tgt aaa atg gaa aaa tgt tcc agt gtg ttt aat gtc gta aat     240
Lys Ile Cys Lys Met Glu Lys Cys Ser Ser Val Phe Asn Val Val Asn
 65                  70                  75                  80 agt aat tct gga tgt ttc aga cat tta gat gaa aga gaa gaa tgt aaa     288
Ser Asn Ser Gly Cys Phe Arg His Leu Asp Glu Arg Glu Glu Cys Lys
                85                  90                  95 tgt tta tta gaa gat tca ggt agc aac gga aag aaa atc aca tgt gaa     336
Cys Leu Leu Glu Asp Ser Gly Ser Asn Gly Lys Lys Ile Thr Cys Glu
            100                 105                 110 tgt act aaa cct gat tct aag cct att gtg caa tat gac aat ttc aat     384
Cys Thr Lys Pro Asp Ser Lys Pro Ile Val Gln Tyr Asp Asn Phe Asn
115                 120                 125 gca aac cca aac gca aac ccc aat gca aat cct gat gga aat tgt gaa     432
Ala Asn Pro Asn Ala Asn Pro Asn Ala Asn Pro Asp Gly Asn Cys Glu
        130                 135                 140 gat ata cca cat gta aat gaa ttt tca gca att gat ctt gga aat gct     480
Asp Ile Pro His Val Asn Glu Phe Ser Ala Ile Asp Leu Gly Asn Ala
145                 150                 155                 160 gaa aaa tat gat aaa atg gat gaa cca caa cat tat ggg aaa tca ctc     528
Glu Lys Tyr Asp Lys Met Asp Glu Pro Gln His Tyr Gly Lys Ser Leu
                165                 170                 175 act cca tta gaa gaa tta tat aaa cca aat gat aaa agt ttg tat cag     576
Thr Pro Leu Glu Glu Leu Tyr Lys Pro Asn Asp Lys Ser Leu Tyr Gln
            180                 185                 190 tat ata aaa gca aat tct aaa ttt ata ggt ata act gaa cta agc aac     624
Tyr Ile Lys Ala Asn Ser Lys Phe Ile Gly Ile Thr Glu Leu Ser Asn
        195                 200                 205 aca ttc ata aac aat gct gga caa cat gga cat atg cat ggt aac gag     672
Thr Phe Ile Asn Asn Ala Gly Gln His Gly His Met His Gly Asn Glu
210                 215                 220 agg gaa gat gag aga acg ctt act aag gaa tat gaa gat att gtt ttg     720
Arg Glu Asp Glu Arg Thr Leu Thr Lys Glu Tyr Glu Asp Ile Val Leu
225                 230                 235                 240 aaa gag ttt aca tat atg ata aac ttt gga aga gga cag aat tat tgg     768
Lys Glu Phe Thr Tyr Met Ile Asn Phe Gly Arg Gly Gln Asn Tyr Trp
                245                 250                 255 gaa cat cca tat caa aaa agt gat caa cct aaa caa tat gaa caa cat     816
Glu His Pro Tyr Gln Lys Ser Asp Gln Pro Lys Gln Tyr Glu Gln His
            260                 265                 270 tta aca gat tat gaa aaa att aaa gaa ggt aag ccc ttg gat aaa ttt     864
Leu Thr Asp Tyr Glu Lys Ile Lys Glu Gly Lys Pro Leu Asp Lys Phe
        275                 280                 285 gga aat atc tat gat tat cac tat gag cat tct agt cca tct agt aca     912
Gly Asn Ile Tyr Asp Tyr His Tyr Glu His Ser Ser Pro Ser Ser Thr
290                 295                 300
```

| aag | tca | tca | agt | cca | tca | aat | gta | aaa | tca | gct | agt | cta | gct | aca | aga | 960 |
| Lys | Ser | Ser | Ser | Pro | Ser | Asn | Val | Lys | Ser | Ala | Ser | Leu | Ala | Thr | Arg | |
| 305 | | | | 310 | | | | 315 | | | | 320 | | | | |

| tta | atg | aaa | aaa | ttt | aaa | gct | gaa | atc | aga | gat | ttc | ttc | ggt | ata | agt | 1008 |
| Leu | Met | Lys | Lys | Phe | Lys | Ala | Glu | Ile | Arg | Asp | Phe | Phe | Gly | Ile | Ser | |
| | | | 325 | | | | 330 | | | | 335 | | | | | |

| tat | tat | gaa | aag | gtt | tta | gcg | aaa | tat | aag | gat | gat | tta | gaa | tag | | 1053 |
| Tyr | Tyr | Glu | Lys | Val | Leu | Ala | Lys | Tyr | Lys | Asp | Asp | Leu | Glu | | | |
| | | | 340 | | | | 345 | | | | 350 | | | | | |

<210> SEQ ID NO 2
<211> LENGTH: 350
<212> TYPE: PRT
<213> ORGANISM: Artificial Sequence
<220> FEATURE:
<223> OTHER INFORMATION: Recombinant DNA/Protein

<400> SEQUENCE: 2

Met Lys Phe Leu Val Asn Val Ala Leu Val Phe Met Val Val Tyr Ile
1               5                   10                  15

Ser Tyr Ile Tyr Ala Asp His His His His His Lys His Lys Lys
            20                  25                  30

Leu Lys Gln Pro Gly Asp Gly Asn Pro Trp Ser Pro Cys Ser Val Thr
        35                  40                  45

Cys Gly Lys Pro Lys Asp Glu Leu Asp Tyr Glu Asn Asp Ile Glu Lys
    50                  55                  60

Lys Ile Cys Lys Met Glu Lys Cys Ser Ser Val Phe Asn Val Val Asn
65                  70                  75                  80

Ser Asn Ser Gly Cys Phe Arg His Leu Asp Glu Arg Glu Cys Lys
            85                  90                  95

Cys Leu Leu Glu Asp Ser Gly Ser Asn Gly Lys Lys Ile Thr Cys Glu
        100                 105                 110

Cys Thr Lys Pro Asp Ser Lys Pro Ile Val Gln Tyr Asp Asn Phe Asn
    115                 120                 125

Ala Asn Pro Asn Ala Asn Pro Asn Ala Asn Pro Asp Gly Asn Cys Glu
130                 135                 140

Asp Ile Pro His Val Asn Glu Phe Ser Ala Ile Asp Leu Gly Asn Ala
145                 150                 155                 160

Glu Lys Tyr Asp Lys Met Asp Glu Pro Gln His Tyr Gly Lys Ser Leu
            165                 170                 175

Thr Pro Leu Glu Glu Leu Tyr Lys Pro Asn Asp Lys Ser Leu Tyr Gln
        180                 185                 190

Tyr Ile Lys Ala Asn Ser Lys Phe Ile Gly Ile Thr Glu Leu Ser Asn
    195                 200                 205

Thr Phe Ile Asn Asn Ala Gly Gln His Gly His Met His Gly Asn Glu
210                 215                 220

Arg Glu Asp Glu Arg Thr Leu Thr Lys Glu Tyr Glu Asp Ile Val Leu
225                 230                 235                 240

Lys Glu Phe Thr Tyr Met Ile Asn Phe Gly Arg Gly Gln Asn Tyr Trp
            245                 250                 255

Glu His Pro Tyr Gln Lys Ser Asp Gln Pro Lys Gln Tyr Glu Gln His
        260                 265                 270

Leu Thr Asp Tyr Glu Lys Ile Lys Glu Gly Lys Pro Leu Asp Lys Phe
    275                 280                 285

Gly Asn Ile Tyr Asp Tyr His Tyr Glu His Ser Ser Pro Ser Ser Thr
290                 295                 300

```
Lys Ser Ser Ser Pro Ser Asn Val Lys Ser Ala Ser Leu Ala Thr Arg
305                 310                 315                 320

Leu Met Lys Lys Phe Lys Ala Glu Ile Arg Asp Phe Phe Gly Ile Ser
            325                 330                 335

Tyr Tyr Glu Lys Val Leu Ala Lys Tyr Lys Asp Asp Leu Glu
        340                 345                 350

<210> SEQ ID NO 3
<211> LENGTH: 16
<212> TYPE: PRT
<213> ORGANISM: Plasmodium falciparum

<400> SEQUENCE: 3

Lys Pro Leu Asp Lys Phe Gly Asn Ile Tyr Asp Tyr His Tyr Glu His
1               5                   10                  15

<210> SEQ ID NO 4
<211> LENGTH: 12
<212> TYPE: PRT
<213> ORGANISM: Plasmodium falciparum

<400> SEQUENCE: 4

Asn Ala Asn Pro Asn Ala Asn Pro Asn Ala Asn Pro
1               5                   10

<210> SEQ ID NO 5
<211> LENGTH: 13
<212> TYPE: PRT
<213> ORGANISM: Plasmodium falciparum

<400> SEQUENCE: 5

Lys His Lys Lys Leu Lys Gln Pro Gly Asp Gly Asn Pro
1               5                   10

<210> SEQ ID NO 6
<211> LENGTH: 23
<212> TYPE: PRT
<213> ORGANISM: Plasmodium falciparum

<400> SEQUENCE: 6

Lys Pro Lys Asp Glu Leu Asp Tyr Glu Asn Asp Ile Glu Lys Lys Ile
1               5                   10                  15

Cys Lys Met Glu Lys Cys Ser
            20

<210> SEQ ID NO 7
<211> LENGTH: 21
<212> TYPE: PRT
<213> ORGANISM: Plasmodium falciparum

<400> SEQUENCE: 7

Asp Ile Glu Lys Lys Ile Cys Lys Met Glu Lys Cys Ser Ser Val Phe
1               5                   10                  15

Asn Val Val Asn Ser
            20

<210> SEQ ID NO 8
<211> LENGTH: 9
<212> TYPE: PRT
<213> ORGANISM: Plasmodium falciparum

<400> SEQUENCE: 8

Trp Ser Pro Cys Ser Val Thr Cys Gly
```

```
1               5

<210> SEQ ID NO 9
<211> LENGTH: 9
<212> TYPE: PRT
<213> ORGANISM: Plasmodium falciparum

<400> SEQUENCE: 9

Lys Pro Ile Val Gln Tyr Asp Asn Phe
1               5

<210> SEQ ID NO 10
<211> LENGTH: 8
<212> TYPE: PRT
<213> ORGANISM: Plasmodium falciparum

<400> SEQUENCE: 10

Lys Pro Asn Asp Lys Ser Leu Tyr
1               5

<210> SEQ ID NO 11
<211> LENGTH: 18
<212> TYPE: PRT
<213> ORGANISM: Plasmodium falciparum

<400> SEQUENCE: 11

Asn Ser Gly Cys Phe Arg His Leu Asp Glu Arg Glu Glu Cys Lys Cys
1               5                   10                  15

Leu Leu

<210> SEQ ID NO 12
<211> LENGTH: 19
<212> TYPE: PRT
<213> ORGANISM: Plasmodium falciparum

<400> SEQUENCE: 12

Glu Asp Ser Gly Ser Asn Gly Lys Lys Ile Thr Cys Glu Cys Thr Lys
1               5                   10                  15

Pro Asp Ser

<210> SEQ ID NO 13
<211> LENGTH: 17
<212> TYPE: PRT
<213> ORGANISM: Plasmodium falciparum

<400> SEQUENCE: 13

Gly Ile Ser Tyr Tyr Glu Lys Val Leu Ala Lys Tyr Lys Asp Asp Leu
1               5                   10                  15

Glu

<210> SEQ ID NO 14
<211> LENGTH: 8
<212> TYPE: PRT
<213> ORGANISM: Plasmodium falciparum

<400> SEQUENCE: 14

Ser Asn Thr Phe Ile Asn Asn Ala
1               5

<210> SEQ ID NO 15
<211> LENGTH: 8
<212> TYPE: PRT
<213> ORGANISM: Plasmodium falciparum
```

-continued

```
<400> SEQUENCE: 15

Gly Gln His Gly His Met His Gly
1               5

<210> SEQ ID NO 16
<211> LENGTH: 18
<212> TYPE: PRT
<213> ORGANISM: Plasmodium falciparum

<400> SEQUENCE: 16

Asp Gly Asn Cys Glu Asp Ile Pro His Val Asn Glu Phe Ser Ala Ile
1               5                   10                  15

Asp Leu

<210> SEQ ID NO 17
<211> LENGTH: 18
<212> TYPE: PRT
<213> ORGANISM: Plasmodium falciparum

<400> SEQUENCE: 17

Gly Asn Ala Glu Lys Tyr Asp Lys Met Asp Glu Pro Gln His Tyr Gly
1               5                   10                  15

Lys Ser

<210> SEQ ID NO 18
<211> LENGTH: 19
<212> TYPE: PRT
<213> ORGANISM: Plasmodium falciparum

<400> SEQUENCE: 18

Asp Gln Pro Lys Gln Tyr Glu Gln His Leu Thr Asp Tyr Glu Lys Ile
1               5                   10                  15

Lys Glu Gly

<210> SEQ ID NO 19
<211> LENGTH: 22
<212> TYPE: PRT
<213> ORGANISM: Plasmodium falciparum

<400> SEQUENCE: 19

Glu Phe Thr Tyr Met Ile Asn Phe Gly Arg Gly Gln Asn Tyr Trp Glu
1               5                   10                  15

His Pro Tyr Gln Lys Ser
            20

<210> SEQ ID NO 20
<211> LENGTH: 19
<212> TYPE: PRT
<213> ORGANISM: Plasmodium falciparum

<400> SEQUENCE: 20

Asn Glu Arg Glu Asp Glu Arg Thr Leu Thr Lys Glu Tyr Glu Asp Ile
1               5                   10                  15

Val Leu Lys

<210> SEQ ID NO 21
<211> LENGTH: 8
<212> TYPE: PRT
<213> ORGANISM: Plasmodium falciparum

<400> SEQUENCE: 21
```

```
Leu Thr Pro Leu Glu Glu Leu Tyr
1               5

<210> SEQ ID NO 22
<211> LENGTH: 17
<212> TYPE: PRT
<213> ORGANISM: Plasmodium falciparum

<400> SEQUENCE: 22

Ser Ser Pro Ser Ser Thr Lys Ser Ser Pro Ser Asn Val Lys Ser Ala
1               5                   10                  15

Ser

<210> SEQ ID NO 23
<211> LENGTH: 17
<212> TYPE: PRT
<213> ORGANISM: Plasmodium falciparum

<400> SEQUENCE: 23

Leu Ala Thr Arg Leu Met Lys Lys Phe Lys Ala Glu Ile Arg Asp Phe
1               5                   10                  15

Phe

<210> SEQ ID NO 24
<211> LENGTH: 15
<212> TYPE: PRT
<213> ORGANISM: Plasmodium falciparum

<400> SEQUENCE: 24

Gln Tyr Ile Lys Ala Asn Ser Lys Phe Ile Gly Ile Thr Glu Leu
1               5                   10                  15

<210> SEQ ID NO 25
<211> LENGTH: 22
<212> TYPE: PRT
<213> ORGANISM: Honey bee

<400> SEQUENCE: 25

Met Lys Phe Leu Val Asn Val Ala Leu Val Phe Met Val Val Tyr Ile
1               5                   10                  15

Ser Tyr Ile Tyr Ala Asp
            20

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

His His His His His His
1               5
```